United States Patent [19]

Cook et al.

[11] Patent Number: 5,459,255

[45] Date of Patent: Oct. 17, 1995

[54] N-2 SUBSTITUTED PURINES

[75] Inventors: P. Dan Cook, Carlsbad; Kanda S. Ramasamy, Laguna Hills; Muthiah Manoharan, Carlsbad, all of Calif.

[73] Assignee: Isis Pharmaceuticals, Inc., Carlsbad, Calif.

[21] Appl. No.: 159,088

[22] Filed: Nov. 29, 1993

Related U.S. Application Data

[60] Continuation-in-part of PCT/US91/00243, Jan. 11, 1991, which is a continuation-in-part of Ser. No. 463,358, Jan. 11, 1990, abandoned, and a continuation-in-part of Ser. No. 566,977, Aug. 13, 1990, abandoned, and a continuation-in-part of Ser. No. 854,634, Jul. 1, 1992, abandoned.

[51] Int. Cl.$^6$ ................................................. C07H 19/00
[52] U.S. Cl. ..................... 536/27.13; 536/27.21; 536/27.6; 536/27.61; 536/27.8; 536/27.81
[58] Field of Search ......................... 536/27.1, 27.11, 536/27.13, 27.21, 23.1, 27.61, 27.8, 27.81

[56] References Cited

U.S. PATENT DOCUMENTS

| | | | |
|---|---|---|---|
| 3,654,262 | 4/1972 | Walton et al. | 536/27.13 |
| 4,804,748 | 2/1989 | Seela | 536/27.13 |
| 5,216,141 | 6/1993 | Benner | 536/27.13 |

OTHER PUBLICATIONS

Beaucage, 3H-1, 2-Benzodithiole-3-one 1,1-Dioxide as an Improved Sulfurizing Reagent in the Solid-Phase Synthesis of Oligeodeoxyribonucleoside Phosphorothioates, *J. Am. Chem. Soc.*, vol. 112, pp. 1253–1255 (1990).

Beaucage et al., Deoxynucleoside Phosphoramidites–A New Class of Key Intermediates for Deoxypolynucleotide Synthesis, *Tetrahedron Letters*, 1981, 22, 1859–1862.

Casale, et al., Synthesis and Properties of an Ogliodeoxynucleotide Containing a Polycyclic Aromatic Hydrocarbon Site Specifically Bound to the $N^2$ Amino Group of a 2'-Deoxyguanosine Residue, *J. Am. Chem. Soc'y*, 1990, 112, 5264–5271.

Cook, P. D., Medicinal chemistry of antisense Oligonucleotides—future opportunities, *Anti-Cancer Drug Design*, 1991, 6, 585–607.

Greene and Wuts, *Protective Groups in Organic Synthesis*, (2nd edition, John Wiley & Sons, New York, 1991.

Harris et al., New Strategy for the Synthesis of Oligodeoxynucleotides Bearing Adducts at Exocyclic Amino Sites of Purine Nucleosides, *J. Am. Chem. Soc'y*, 1991, 113, 4328–4329.

Inoue, Synthesis and hybridization studies on two complementary nona(2'-O-methyl)ribonucleotides, et al., *Nucleic Acids Res. 1987, 15, 6131*.

Johnson et al., Site-Specific Adduct Formation in Oligomeric DNA Using a New Protecting Group, *J. Am. Chem. Soc'y*, 1992, 114, 4923–4924.

Kawasaki, et al., Synthesis and Biophysical Stuides of 2'-dRIBO-2'-F. Modified Oligonucleotides, *J. Med. Chem.*, in press 1993.

Lee et al., Syntheses of Polycyclic Aromatic Hydrocarbon–Nucleoside and Oligonucleotide Adducts Specifically Alklyated on the Amino Functions of Deoxyguanosine and Deoxyagenosine, *Tetrahedron Letters*, 1990, 31, 6773–6776.

Miller, et al., A new approach to chemotherapy based on molecular biology and nucleic acid chemistry: Matagen (masking tape for gene expression), *Anti-Cancer Drug Design*, 1987, 2, 117–128.

M. S. Motawai et al., A new Route to 2', 3'-Dideoxycytidine, *Liebigs Ann. Chem.*, 1990, 599–602.

Uhlmann, et al., Antisense Oligonucleotides: A New Therapeutic Principle, *Chem. Rev.*, 1990, 90, 4, 553–584.

Walder, Antisense DNA and RNA: progress and prospects, *Genes & Development*, 1988, 2 502–504.

*Primary Examiner*—Douglas W. Robinson
*Assistant Examiner*—James O. Wilson
*Attorney, Agent, or Firm*—Woodcock Washburn Kurtz Mackiewicz & Norris

[57] ABSTRACT

This invention presents novel purine-based compounds for inclusion into oligonucleotides. The compounds of the invention, when incorporated into oligonucleotides are especially useful as agents that are capable of specific hybridization with a nucleotide sequence of an RNA. Oligonucleotides are used for a variety of purposes, such as regulating gene expression in experimental systems, assaying for RNA and for RNA products through the employment of interactions with such RNA, diagnosing diseases, modulating the production of proteins, and cleaving RNA in site specific fashions. The compounds of the invention include novel heterocyclic bases, nucleosides, and nucleotides. When incorporated into oligonucleotides, the compounds of the invention can be useful for modulating the activity of RNA.

27 Claims, No Drawings

N-2 SUBSTITUTED PURINES

RELATED APPLICATIONS

This application is a continuation-in-part of PCT International Patent Application No. PCT\US91\00243, filed Jan. 11, 1991, which published as WO 91/10671 on Jul. 25, 1991, and its corresponding National Phase U.S. patent application Ser. No. 854,634, filed Jul. 1, 1992, now abandoned, both of which are continuation-in-part applications of U.S. patent Ser. No. 463,358 filed Jan. 11, 1990, now abandoned, U.S. patent application Ser. No. 566,977 filed Aug. 13, 1990, now abandoned, and U.S. Patent application Ser. No. 854,634, filed Jul. 1, 1992, now abandoned.

FIELD OF THE INVENTION

This invention relates to novel purine-based compounds that may be incorporated into oligonucleotides. Oligonucleotides are used for a variety of diagnostic purposes, such as, regulating gene expression in experimental systems, assaying for RNA and for RNA products through interactions with such RNA, diagnosing diseases, modulating the production of proteins, and cleaving RNA in site specific fashions. The compounds of the invention include novel heterocyclic bases, nucleosides, and nucleotides. When incorporated into oligonucleotides, the compounds of the invention are useful for modulating the activity of RNA.

BACKGROUND OF THE INVENTION

It is well known that most of the bodily states in mammals including most disease states, are affected by proteins. Such proteins, either acting directly or through their enzymatic functions, contribute in major proportion to many diseases in animals and man. Classical therapeutics has generally focused on interactions with such proteins in efforts to moderate their disease causing or disease potentiating functions. Recently, however, attempts have been made to moderate the actual production of such proteins by interactions with molecules that direct their synthesis, such as intracellular RNA. By interfering with the production of proteins, it has been hoped to affect therapeutic results with maximum effect and minimal side effects. It is the general object of such therapeutic approaches to interfere with or otherwise modulate gene expression leading to undesired protein formation.

One method for inhibiting specific gene expression is the use of oligonucleotides and oligonucleotide analogs as "antisense" agents. The oligonucleotides or oligonucleotide analogs complimentary to a specific, target, messenger RNA (mRNA) sequence are used. Antisense methodology is often directed to the complementary hybridization of relatively short oligonucleotides and oligonucleotide analogs to single-stranded mRNA or single-stranded DNA such that the normal, essential functions of these intracellular nucleic acids are disrupted. Hybridization is the sequence specific hydrogen bonding of oligonucleotides or oligonucleotide analogs to Watson-Crick base pairs of RNA or single-stranded DNA. Such base pairs are said to be complementary to one another. The oligonucleotides and oligonucleotide analogs are intended to inhibit the activity of the selected mRNA—to interfere with translation reactions by which proteins coded by the mRNA are produced—by any of a number of mechanisms. The inhibition of the formation of the specific proteins that are coded for by the mRNA sequences interfered with have been hoped to lead to therapeutic benefits. Cook, P. D. *Anti-Cancer Drug Design* 1991, 6,585; Cook, P. D. *Medicinal Chemistry Strategies for Antisense Research, in Antisense Research & Applications*, Crooke, et al., CRC Press, Inc.; Boca Raton, Fla., 1993; Uhlmann, et al., *A. Chem. Rev.* 1990, 90,543.

A serious deficiency of unmodified oligonucleotides for these purposes, is the enzymatic degradation of the oligonucleotides by a variety of intracellular and extracellular ubiquitous nucleolytic enzymes, hereinafter referred to as "nucleases."

Initially, only two mechanisms or terminating events have been thought to be operating in the antisense approach to therapeutics. These are the hybridization arrest mechanism and the cleavage of hybridized RNA by the cellular enzyme, ribonuclease H (RNase H). Cook, 1991, supra; Cook, 1993, supra; Uhlmann, supra; Walder, et al., *Proc. Natl. Acad. Sci., USA*, 1988, 85, 5011; Dagle, et al., *Antisense Research & Development*, 1991, 1, 11. It is likely, however, that additional "natural" events may be involved in the disruption of targeted RNA. Many of these naturally occurring events are discussed in *Oligonucleotides: Antisense Inhibitors of Gene Expression*, CRC Press, Inc., Boca Raton, Fla. (Cohen ed., 1989).

Hybridization arrest denotes the terminating event in which the oligonucleotide inhibitor binds to the target nucleic acid and thus prevents, by simple steric hindrance, the binding of essential proteins, most often ribosomes, to the nucleic acid. Methyl phosphonate oligonucleotides, Miller, et al., *Anti-Cancer Drug Design*, 1987, 2, 117–128, and α-anomer oligonucleotides are two extensively studied antisense agents that are thought to disrupt nucleic acid function by hybridization arrest.

The second "natural" type of terminating event is the activation of RNase H by the heteroduplex formed between the DNA type oligonucleotides or oligonucleotide analogs and the targeted RNA with subsequent cleavage of target RNA by the enzyme. The oligonucleotides or oligonucleotide analogs, which must be of the deoxyribose type, hybridize with the targeted RNA and this duplex activates the RNase H enzyme to cleave the RNA strand, thus destroying the normal function of the RNA. Phosphorothioate modified oligonucleotides are the most prominent example of antisense agents that are thought to operate by this type of antisense terminating event. Walder, supra and Stein, et al., *Nucleic Acids Research*, 1988, 16, 3209–3221 describe the role that RNase H plays in the antisense approach.

A number of chemical modifications have been introduced into antisense agents—oligonucleotides and oligonucleotide analogs—to increase their activity. Such modifications are designed to increase cell penetration of the antisense agents, to stabilize the antisense agents from nucleases and other enzymes that degrade or interfere with their structure or activity, to enhance the antisense agents' binding to targeted RNA, and to provide a mode of disruption (terminating event) once the antisense agents are sequence-specifically bound to targeted RNA, and to improve the antisense agents' pharmacokinetic and phamacodynamic properties.

To increase the potency via the "natural" termination events, the most often used oligonucleotide modification is modification at the sugar-phosphate backbone, particularly on the phosphorus atom. Phosphorothioates, methyl phosphonates, phosphoramidites, and phosphotriesters have been reported to have various levels of resistance to nucleases. However, all reported modifications of the sugar-phosphate backbone, with the exception of phosphorothioates and phosphorodithioates, obliterate the RNase H terminating event. Cook, 1991, supra; Cook, 1993, supra; Uhlmann, supra. Heteroduplexes formed between RNA and oligodeoxynucleotides bearing 2'-sugar modifications, RNA mimics such as fluoro and alkoxys, do not support RNase H-mediated cleavage. These modified heteroduplexes assume an A form helical geometry as does RNA-RNA heteroduplexes which also do not support RNase H cleavage. Kawasaki, et al., *J. Med. Chem.*, in press 1993; Lesnik, et al., *Biochemistry*, submitted 1993; Inoue, et al., *Nucleic Acids Res.*, 1987, 15, 6131.

Other modifications to "wild type" oligo-nucleotides made to enhance resistance to nucleases, activate the RNase terminating event, or enhance the RNA-oligonucleotide duplex's hybridization properties include functionalizing the nucleoside's naturally occurring sugar. Sugar modifications are disclosed as set forth in PCT Application assigned to a common assignee hereof, entitled "Compositions and Methods for Detecting and Modulating RNA Activity and Gene Expression," PCT Patent Application Number PCT\US91\00243, International Publication Number WO 91/10671, the disclosures of which are incorporated herein by reference to disclose more fully such modifications.

Other synthetic terminating events, as compared to hybridization arrest and RNase H cleavage, have been studied in an attempt to increase the potency of oligonucleotides and oligonucleotide analogs for use in antisense diagnostics and therapeutics. One area of research is based on the concept that antisense oligonucleotides with modified heterocyclic portions, rather than sugar-phosphate modifications, can be resistant to nucleolytic degradation, yet on hybridization to target RNA provide a heteroduplex that supports RNase H-mediated cleavage. Modifications in the heterocycle portion of oligonucleotides may not affect the heteroduplex helical geometry of sugar that is necessary for RNase H cleavage.

Accordingly, there remains a great need for antisense oligonucleotide compositions that are capable of improved specificity and effectiveness both in binding and modulating mRNA modulation or inactivating mRNA without imposing undesirable side effects. The present invention addresses these, as well as other, needs by presenting novel compounds, based on the purine ring system, that may be used as oligonucleotide intermediates. It has now been found that certain positions on the nucleosides of double stranded nucleic acids are exposed in the minor groove and may be substituted without affecting Watson-Crick base-pairing or duplex stability. Reactive or non-reactive functionalities placed in these positions can best initiate cleavage and destruction of targeted RNA or interfere with its activity.

SUMMARY OF THE INVENTION

This invention presents novel compounds based on the purine ring system that have utility as intermediates for the synthesis of oligonucleotides and oligonucleotide analogs. This invention presents novel, substituted purines comprising a tether portion and at least one reactive or non-reactive functionality. In particular, this invention provides nucleosides, nucleoside analogs, nucleotides, nucleotide analogs, heterocyclic bases, heterocyclic base analogs based on the purine ring system, and oligonucleotide compositions incorporating the same.

The heterocyclic compounds of the invention are adapted for placement of the reactive, RNA cleaving moiety or other reactive moiety into the minor groove site of the hybrid structure formed from the RNA and the compositions of the invention through careful selection of the attachment of the RNA cleaving moieties.

The 2 position of the purine ring has now been found to be a site for attachment of potential RNA cleaving moieties as well as other moieties that may enhance pharmacokinetic properties without affecting RNase H degradation of target RNA. In addition, a remarkable enhancement of heteroduplex binding affinity is observed when certain pendent groups are attached to the 2 position of the novel purine based compounds of the invention. These pendent groups protrude into the minor groove of a DNA-RNA heteroduplex and do not affect binding affinities.

In one aspect of the invention, the compounds have the formula:

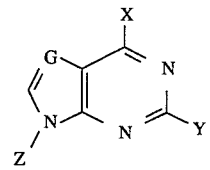

wherein
G is C or N;
X is $NH_2$ or OH;
Y is RQ or NHRQ, wherein R is a hydrocarbyl group having from 2 to about 20 carbon atoms; and Q is at least one reactive or nonreactive functionality; and
Z is H, a nitrogen protecting group, or a sugar moiety.

The invention further provides compounds comprising a sugar and base moiety as discussed above, with the 3' position of the sugar moiety derivatized with a phosphate group. The sugar moiety of the nucleosidic units for incorporation into oligonucleotides compositions may be ribose, deoxyribose, or a sugar analog. Preferably the sugar is ribose or deoxyribose. The groups linking the heterocyclic bases or modified bases together may be the usual sugar phosphate nucleic acid backbone found in nature, but may also be modified as a phosphorothioate, methylphosphonate, or phosphate alkylated moiety to further enhance the modified oligonucleotides' properties. Other backbone modifications may also be employed such as the removal of 5'-methylene group, and the use of alkyl, or heteroatomic sugar.

In another aspect of this invention, mixed sequence oligonucleotides incorporating at least one of the compounds as set forth herein are presented.

DETAILED DESCRIPTION OF PREFERRED EMBODIMENTS

This invention presents novel heterocyclic compounds based on the purine ring system that may be used as intermediates for oligonucleotide compositions. This invention provides nucleosides, nucleoside analogs, nucleotides, nucleotide analogs, heterocyclic bases, heterocyclic base analogs, and oligonucleotide compositions incorporating the same.

The novel compounds of the invention are based on the purine ring system, comprising a heterocyclic purine-base portion, at least one reactive or non-reactive functionality, and a tether portion for attaching the functionalities to the balance of the compound. The 2 position of the purine ring has been found to be a unique point of attachment for reactive and non-reactive functionalities. Attachment at this position enhances the oligonucleotides and oligonuceltides analogs' ability to modulate RNA activity without interfering with stability of an RNA-oligonucleotide heteroduplex, and also improves the oligonucleotides' transport properties. The non-reactive functionalities' utility lies, in part, in their ability to improve the pharmacodynamic or pharmacokinetic properties of the oligonucleotide compositions, whether or not these functionalities may also play a role in initiating cleaving reactions. These attributes and others make these compounds useful intermediates for incorporation into oligonucleotide compositions.

The functional sites on the base units are important in the design of compositions for sequence-specific destruction or modulation of targeted RNA. The half-life of the formed duplex is believed to be greatly effected by the positioning of the tethered group that connects the reactive functionality to the base unit. Inappropriate positioning of functional groups, such as placement on the Watson-Crick base pair sites, would preclude duplex formation. It is important that the tether functionality not interfere with Watson-Crick base pair hydrogen bonding rules as this is the sequence-specific recognition/binding factor for selection of the desired RNA to be disrupted.

Attachment sites, other than the 2 position of the purine ring, may allow sequence-specific binding but may be of such low stability that the reactive functionality will not have sufficient time to initiate RNA disruption. It has now been found that certain positions on the nucleosides of double stranded nucleic acids are exposed in the minor groove and may be substituted without affecting Watson-Crick base-pairing or duplex stability. Reactive or non-reactive functionalities placed in these positions in accordance with this invention can best initiate cleavage and destruction of targeted RNA or interfere with its activity. The sites of functionality in the heterocyclic compounds of the invention are novel—the 2 position of the purine ring system—and have been preferably designed such that the functionalities will preferably reside in or on the minor groove formed by the heteroduplex between modified oligonucleotides and targeted RNA.

The compounds of the invention may have at least one reactive functionality or other moiety appended thereto capable of interacting with, preferably cleaving, an RNA. These moieties are preferably adapted for placement of the reactive or other moiety into the minor groove site of the hybrid structure formed from the RNA and oligonucleotides and oligonucleotide analogs including the compositions of the invention.

It is not necessary to tether more than one, two, or a relatively small number of RNA cleaving functionalities to oligonucleotide compositions in accordance with this invention to provide the benefits of the invention. An RNA cleaving moiety will preferably be tethered to a relatively small proportion of the subunits, generally only one or two of the oligonucleotide compositions of the invention. In other embodiments of the invention, however, substantially all of the nucleotides in an oligonucleotide can be modified to include one or more functionalities such as RNA cleaving moieties.

The compounds of the invention may be used to prepare desired oligonucleotides and oligonucleotide analogs; these oligonucleotides and oligonucleotide analogs are also within the ambit of this invention.

Incorporation of the novel compounds of the invention into oligonucleotide compositions improves those compositions' pharmacokinetic and pharmacodynamic properties, the compositions' resistance to nucleases, facilitates uses, for example diagnostic uses, and research reagent uses, improves the compositions' binding capabilities without any concomitant interference with the Watson-Crick binding, and enhances the compositions' penetration into cells. Some of these enhanced properties are illustrated in Table 1 below.

In the context of this invention, a "nucleoside" is a nitrogenous heterocyclic base linked to a pentose sugar, either a ribose, deoxyribose, or derivatives or analogs thereof. The term "nucleotide" means a phosphoric acid ester of a nucleoside comprising a nitrogenous heterocyclic base, a pentose sugar, and one or more phosphate or other backbone forming groups; it is the monomeric unit of an oligonucleotide. The term "oligonucleotide" refers to a plurality of joined nucleotide units formed in a specific sequence from naturally occurring heterocyclic bases and pentofuranosyl equivalent groups joined through phosphorodiester or other backbone forming groups. Nucleotide units may include the common bases such as guanine, adenine, cytosine, thymine, or derivatives thereof. The pentose sugar may be deoxyribose, ribose, or groups that substitute therefore. The term "oligonucleotide compositions" as used in the context of this invention encompass oligonucleotides and oligonucleotide analogs and are interchangeable. In the context of this invention, phosphate derivatives include phosphorothioates, methyl phosphonates, phosphoramidites, phosphorotriesters, and any other groups known to those skilled in the art.

"Modified base," "base analog," "modified nucleoside," "nucleotide analog," or "modified nucleotide," in the context of this invention refer to moieties that function similarly to their naturally occurring counterparts but have been functionalized to change their properties.

"Sugar moiety," as used in the context of this invention, refers to naturally occurring sugars, such as ribose or deoxyribose, and sugars and non-sugar analogs that have functionalized to change certain properties.

"Oligonucleotide analogs" or "modified oligonucleotides," as used in connection with this invention, refer to compositions that function similarly to natural oligonucleotides but have non-naturally occurring portions. Oligonucleotide analogs or modified oligonucleotides may have altered sugar moieties, altered bases, both altered sugars and bases or altered inter-sugar linkages, for example phosphorothioates and other sulfur containing species which are known for use in the art.

In the context of the invention, "improved pharmacodynamic property" means improved oligonucleotide uptake, enhanced oligonucleotide resistance to degradation, and/or strengthened sequence-specific hybridization with RNA. "Improved pharmacokinetic property" means improved oligonucleotide uptake, distribution, metabolism, or excretion.

The "hydrocarbyl" groups disclosed and claimed herein are the linkers or tethers that attach reactive or non-reactive functionalities to the purine based compounds of the invention. "Hydrocarbyl compounds," as used herein, means straight, branched, or cyclic carbon and hydrogen containing compounds. In the context of this invention, a straight chain compound means an open chain compound, such as an aliphatic compound, including alkyl, alkenyl, or alkynyl compounds. A branched compound, as used herein, comprises a straight chain compound, such as an alkyl, alkenyl, alkynyl, which has further straight chains attached to the carbon atoms of the straight chain. In the context of this invention, the terms "lower alkyl," "lower alkenyl," or "lower alkynl" means compounds, straight or branched, having between about 1 to about 10 carbon atoms. A "cyclic compound," as used herein, refers to closed chain compounds—is, a ring of carbon atoms, such as a cyclic aliphatic or aromatic compound. The straight, branched, or cyclic compounds may be internally interrupted. In the context of this invention, internally interrupted means that the carbon chains may be interrupted with heteroatoms such as O, N, or S. If desired, the carbon chain may have no heteroatoms present. The hydrocarbyl compounds noted above may be substituted or unsubstituted. In the context of this invention, "substituted" or "unsubstituted," means that the hydrocarbyl compounds may have any one of a variety of substituents, in replacement, for example, of one or more hydrogen atoms in the compound, or may have no substituents. Suitable substituents will be readily apparent to one skilled in the art once armed with the present disclosure.

Pendent groups as used herein refers to both reactive and non-reactive functionalities. "Reactive functionality," as used herein, means a moiety that interacts with mRNA in some manner to more effectively inhibit translation of the mRNA into protein. For example, such a moiety may act as an RNA cleaving agent. A "non-reactive functionality," as used herein, means a functional group that may not possess a reactive portion or may not initiate chemical reactions, but rather enhances the oligonucleotide compositions' pharmacodynamic and pharmacokinetic properties, whether or not it plays any role in RNA cleavage. When terminal end is used in reference to the reactive or non-reactive functionality, this term means the end not attached to the purine core.

In one preferred aspect of the invention, the compound has the following formula:

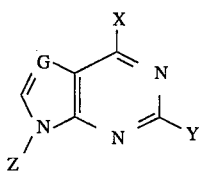

wherein

G is C or N;

X is NH$_2$ or OH;

Y is RQ or NHRQ, wherein said R is H or a hydrocarbyl group having from 2 to about 20 carbon atoms; and Q comprises at least one reactive or non-reactive functionality; and Z is H, a nitrogen protecting group, or a sugar moiety.

In certain preferred embodiments, Q is a nitrogen-containing heterocycle. In other preferred embodiments, Q is a substituted or unsubstituted imidazole. In other more preferred embodiments, Y is RQ and said Q is an imidazole. In still other preferred embodiments, Y is NHRQ and Q is an imidazole.

In certain other preferred embodiments, G is N; X is NH$_2$; Y is NHRQ, said R is a lower alkane and Q is an imidazole. In a more preferred embodiment, R is an alkane having between about 2 to about 4 carbon atoms, preferably propyl.

In other preferred embodiments, G is N; X is OH; Y is NHRQ, said R is a lower alkane; and Q is an imidazole. In more preferred embodiments, R is an alkane having between about 2 to about 4 carbon atoms, preferably ethyl or isobutyryl, more preferably propyl. In other preferred embodiments, R is isobutyryl and Q is a methyl-imidazole.

In still other preferred embodiments, G is N; X is NH$_2$; Y is NHRQ, said R is H and Q is an alkane having from about 5 up to about 20 carbon atoms, preferably between about 5 to about 10 carbon atoms.

In still other preferred embodiments, G is N; X is OH$_2$; Y is NHRQ, said R is H and Q is an alkane having from about 5 up to about 20 carbon atoms, preferably between about 5 to about 10 carbon atoms.

In other certain preferred embodiments, Y is RQ, said R is a lower alkane; and Q is an amine, wherein said amine comprises NH$_2$, polyalkylamines, aminoalkylamines, hydrazines (—NH—NH—), hydroxylamines (—NH—OH), semicarbazides (—NH—C(O)—NH—NH$_2$), thiosemicarbazides (—NH—C(S)—NH—NH$_2$), hydrazones (—N=NH), or hydrazides (—C(O)—NHNH$_2$); and Z is ribose or deoxyribose, preferably deoxyribose.

In other preferred embodiments, Y is NHRQ, said R is a lower alkane; and Q is an amine, wherein said amine comprises NH$_2$, polyalkylamines, aminoalkylamines, hydrazines (—NH—NH—), hydroxylamines (—NH—OH), semicarbazides (—NH—C(O)— NH—NH$_2$), thiosemicarbazides (—NH—C(S)—NH—NH$_2$), hydrazones (—N=NH), or hydrazides (—C(O)—NHNH$_2$); and Z is ribose or deoxyribose.

In a more preferred embodiment, G is N; X is NH$_2$; Y is NHRQ, said R is a lower alkane; and Q is an amine, wherein said amine comprises NH$_2$, polyalkylamines, aminoalkylamines, hydrazines (—NH—NH—), hydroxylamines (—NH—OH), semicarbazides (—NH—C(O)—NH—NH$_2$), thiosemicarbazides (—NH—C(S)—NH—NH$_2$), hydrazones (—N=NH), or hydrazides (—C(O)—NHNH$_2$), especially NH$_2$.

In another preferred embodiment, G is N; X is OH; Y is NHRQ, said R is a lower alkane; and Q is an amine, wherein said amine comprises NH$_2$, polyalkylamines, aminoalkylamines, hydrazines (—NH—NH—), hydroxylamines (—NH—OH), semicarbazides (—NH—C(O)—NH—NH$_2$), thiosemicarbazides (—NH—C(S)—NH—NH$_2$), hydrazones (—N=NH), or hydrazides (—C(O)—NHNH$_2$), especially NH$_2$. In a more preferred embodiment, G is N; X is OH; Y is NHRQ, said R is hexane and Q is NH.

In certain other preferred embodiments, Y is NHRQ, and the reactive functionality, Q, is a thiol group, aldehyde, ketone, alcohol, or an alkoxy group. In other preferred embodiments, Y is RQ and the reactive functionality Q is a thiol group, aldehyde, ketone, alcohol, or an alkoxy group.

The hydrocarbyl groups (R) may serve as tethers or linkers for attaching reactive or non-reactive functionalities to the purine ring system of the compounds of the invention. The hydrocarbyl groups, R, suitable for practicing this invention may be alkyl, alkenyl, aryl, or cyclic groups. Alkyl groups of the invention include, but are not limited to, straight and branched chained alkyls such as methyl, ethyl, propyl, butyl, pentyl, hexyl, heptyl, octyl, nonyl, decyl, undecyl, dodecyl, isopropyl, 2-butyl, isobutyl, 2-methylbutyl, isopentyl, 2-methyl-pentyl, 3-methylpentyl, 2-ethylhexyl, 2-propylpentyl. While propyl groups have been found to be highly useful R groups, other alkyl groups, including methyl, ethyl, butyl, and others up to about octyl, can find utility; preferred are C$_2$ to C$_4$ alkyl with propyl being most preferred. Ethylene, propylene, and other glycols and polyamines are also useful.

Alkenyl groups useful in the invention include, but are not limited to, unsaturated moieties derived from the above alkyl groups including but not limited to vinyl, allyl, crotyl, propargyl.

Useful aryl groups include, but are not limited to, phenyl, tolyl, benzyl, naphthyl, anthracyl, phenanthryl, and xylyl.

Any of the hydrocarbyl groups, that is, the straight, branched, or cyclic alkyl, alkenyl, or alkynyl groups pointed out above may be internally interrupted with heteroatoms, such as O, N, or S; however, this is not required. For example, polyoxyhydrocarbyl or polyaminohydrocarbyl compounds are fully contemplated within the ambit of the invention. Some further examples include those where R may comprise a polyhydric alcohol, such as —CH$_2$—(CHOH)$_n$— CH$_2$OH, wherein n=1 to 5. Alternatively, by way of example, R may comprise an ether, such as —CH$_2$(CHOH)$_n$CH$_2$O(CH$_2$)$_m$, where n=1 to 10 and m=1 to 10.

The hydrocarbyl groups may be further substituted. Substituent groups for the above include, but are not limited to, other alkyl, haloalkyl, alkenyl, alkoxy, thioalkoxy, haloalkoxy and aryl groups as well as halogen, hydroxyl, amino, azido, carboxy, cyano, nitro, mercapto, sulfides, sulfones, sulfoxides, and heterocycles. Other suitable substituent groups will be apparent to those skilled in the art and may be used without departing from the spirit of the invention.

Reactive functionalities suitable for use as Q in the practice of this invention include, but are not limited to, halogens; substituted or unsubstituted heterocyclic compounds, such as substituted or unsubstituted heterocycloalkyls; amino containing groups, such as heterocycloalkylaminos, polyalkylaminos, imidazoles, imadiazole amides, alkylimidazoles; substituted or unsubstituted aldehydes; substituted or unsubstituted ketones; substituted or unsubstituted ethers; substituted or unsubstituted esters; substituted or unsubstituted aryl compounds having from about 6 to about 20 carbon atoms, such as aralkylamino having from about 6 to about 20 carbon atoms, aminoaralkylamino having from about 6 to about 20 carbon atoms, alkyloxyaryl compounds, or allyloxyaryl compounds.

The amine functionalities can be primary amines, hydrazines (—NH—NH—), hydroxylamines (—NH—OH), semicarbazides (—NH—C(O)—NH—NH), thiosemicarbazides (—NH—C(S)—NH—NH$_2$), hydrazones (—N=NH), or hydrazides (—C(O)—NHNH$_2$), or similar nitrogenous species. Amines of this invention are also meant to include polyalkylamino compounds and aminoalkylamines such as aminopropylamines and further heterocycloalkylamines, such as imidazol-1, 2, or 4-yl-propylamine.

Polyamides, polyesters, and polyethylene glycols according to the invention have structures analogous to the above-described polyamines, except that an amide, ester or alcohol functionality is substituted for the nitrogenous species of the polyamine. Polyether groups have also analogous structures, except that one or more ether oxygen atoms are interspersed in the carbon chains.

The following compounds for forming compounds with amine-functionalized linker or tether groups are commercially available from Aldrich Chemical Co., Inc., Milwaukee, Wis.: N-(2-bromethyl)phthalimide, N-(3-bromopropyl)phthalimide and N-(4-bromobutyl)phthalimide. Other phthalimide-protected amine compounds can be conveniently synthesized from appropriate alkyl, aralkyl or aryl halides and phthalimide. Representative compounds include N-(7-bromoheptyl)phthalimide; N-(8-bromooctyl)phthalimide; N-(9-bromononyl)phthalimide; N-(10-bromododecyl)phthalimide; N-(11-bromoundecyl)phthalimide; N-(12-bromodocecyl)phthalimide; N-(13-bromotridecyl)phthalimide; N-(14-bromotetradecyl)phthalimide; N-(15-bromopentadecyl)phthalimide; N-(16-bromohexadecyl)phthalimide; N-(17-bromoheptadecyl)phthalimide; N-(18-bromooctadecyl)phthalimide; N-(19-bromononadecyl)phthalimide; N-(3-bromo-2-methylpropyl)phthalimide; N-(4-bromo-2-methyl-3-ethylbutyl)phthalimide; N-(3-bromo-2,2-diethylpropyl)phthalimide; N-(4-bromo-3-propylbutyl)phthalimide; N-(10-bromo-2,8-dibutyldecyl)phthalimide; N-(8-bromo-6,6-dimethyloctyl)phthalimide; N-(8-bromo-6-propyl-6-butyloctyl)phthalimide; N-(4-bromo-2-methylbutyl)phthalimide; N-(5-bromo-2-methylpentyl)phthalimide; N-(5-bromo-3-methylpentyl)phthalimide; N-(6-bromo-2-ethylhexyl)phthalimide; N-(5-bromo-3-penten-2-one)phthalimide; N-(4-bromo-3-methyl-2-butanol)phthalimide; N-(8-bromo-3-amino-4-chloro-2-cyano-octyl)phthalimide; N-(7-bromo-3-methoxy-4-heptanal)phthalimide; N-(4-bromo-2-iodo-3-nitrobutyl)phthalimide; N-(12-bromo-4-isopropoxydodecyl)phthalimide; N-(10-bromo-4-azido-2-nitrodecyl)phthalimide; N-(9-bromo-5-mercaptononyl)phthal- imide; N-(5-bromo-4-amino-pentenyl)phthalimide; N-(5-bromo-penten-2-yl)phthalimide; N-(3-bromoallyl)phthalimide; N-(4-bromocrotyl)phthalimide; N-(3-bromopropargyl)phthalimide; N-(1-bromonaphth-4-yl)phthalimide; N-(2-bromoanthrac-7-yl)-phthalimide; and N-(2-bromophenanthr-6-yl)phthalimide. Such halide compounds are then reacted with an appropriate 2 amino or other 2-substituted purine.

Suitable heterocyclic groups include, but are not limited to, imidazole, tetrazole, triazole, pyrrolidine, piperidine, piperazine and morpholine. Amines include amines of all of the above alkyl, alkenyl and aryl groups including primary and secondary amines and "masked amines" such as phthalimide. Other reactive functionalities suitable for practicing the invention include, without limitation, compounds having thiol (SH), aldehyde (C=O), or alcohol (OH) functionalities.

These reactive functionalities are capable of catalyzing, alkylating, or otherwise effecting the cleavage, destruction or disablement of RNA, especially of its phosphorodiester bonds. The reactive functionalities may either be basic, acidic, or amphoteric. Heteroatomic species can be formulated to be either basic or acidic or, indeed, to be amphoteric for such purposes. Alkylating and free radical forming functionalities may also be used for these purposes.

Non-reactive functionalities for Q, include, but are not limited to, alkyl chains, polyamines, ethylene glycols, polyamides, aminoalkyl chains, amphipathic moieties, points for reporter group attachment, and intercalators attached to any of the preferred sites for attachment.

The reactive and non-reactive functionalities may be further substituted. Suitable substituents include, but are not limited to, other hydrocarbyl compounds, halohydrocarbyl compounds, alkoxy, thioalkoxy, haloalkoxy, or aryl groups, as well as halogen, hydroxyl, amino, azido, carboxy, cyano, nitro, mercapto, sulfides, sulfones and sulfoxides. Any of the straight, branched, or cyclic hydrocarbyl substituents may be further internally interrupted with O, N, or S. Substituent groups can be present on the above-described alkyl, alkenyl, alkyne, polyamine, polyamide, polyester, polyethylene glycol, polyether, aryl, aralkyl and heterocyclic space-spanning groups. Substituent groups include but are not limited to halogen, hydroxyl, keto, carboxy, nitrates, nitrites, nitro, nitroso, nitrile, trifluoromethyl, 0-alkyl, S-alkyl, NH-alkyl, amino, azido, sulfoxide, sulfone, sulfide, silyl, intercalators, conjugates, polyamines, polyamides, polyethylene glycols, polyethers, groups that enhance the pharmacodynamic properties of oligonucleotides and groups that enhance the pharmacokinetic properties of oligonucleotides. Typical intercalators and conjugates include cholesterols, phospholipids, biotin, phenanthroline, phenazine, phenanthridine, anthraquinone, acridine, fluoresceins, rhodamines, coumarins, and dyes. Halogens include fluorine, chlorine, bromine, and iodine. Other suitable substituent groups will be apparent to those skilled in the art and may be used without departing from the spirit of the invention.

The invention further provides compounds comprising a sugar combined with a base moiety as discussed above. Suitable sugar moieties include, but are not limited to, ribose, deoxyribose, and sugar analogs.

In certain preferred embodiments, Z is ribose or deoxyribose. In a more preferred embodiment, Z is deoxyribose. In another preferred embodiment, Z is a sugar analog, preferably similar to the deoxyribose type.

In other preferred embodiments, G is N; X is OH; Y is NHRQ, said R is a lower alkane; and Q is an imidazole; and Z is ribose or deoxyribose, preferably deoxyribose. In more preferred embodiments, R is an alkane having between about 2 to about 4 carbon atoms, preferably ethyl or isobutyryl, more preferably propyl; and Z is ribose or deoxyribose, preferably deoxyribose. In other preferred embodiments, R is isobutyryl and Q is a methyl-imidazole; and Z is ribose or deoxyribose, preferably deoxyribose.

In still other preferred embodiments, G is N; X is $NH_2$; Y is NHRQ, said R is H and Q is an alkane having from about 5 up to about 20 carbon atoms, preferably between about 5 to about 10 carbon atoms; and Z is ribose or deoxyribose, preferably deoxyribose.

In other certain preferred embodiments, Y is RQ, said R is a lower alkane; and Q is an amine, wherein said amine comprises $NH_2$, polyalkylamines, aminoalkylamines, hydrazines (—NH—NH—), hydroxylamines (—NH—OH), semicarbazides (13 NH—C(O)—NH—$NH_2$), thiosemicarbazides (—NH—C(S)—NH—$NH_2$), hydrazones (—N=NH), or hydrazides (—C(O)—NH—$NH_2$); and Z is ribose or deoxyribose, preferably deoxyribose.

In other preferred embodiments, Y is NHRQ, said R is a lower alkane; and Q is an amine, wherein said amine comprises $NH_2$, polyalkylamines, aminoalkylamines, hydrazines (—NH—NH—), hydroxylamines (—NH—OH), semicarbazides (—NH—C(O)— NH—$NH_2$), thiosemicarbazides (—NH—C(S)—NH—$NH_2$), hydrazones (—N=NH), or hydrazides (—C(O)—NH—NH); and Z is ribose or deoxyribose.

In a more preferred embodiment, G is N; X is $NH_2$; Y is NHRQ, said R is a lower alkane; and Q is an amine, wherein said amine comprises $NH_2$, polyalkylamines, aminoalkylamines, hydrazines (—NH—NH—), hydroxylamines (—NH—OH), semicarbazides (—NH—C(O)—NH—$NH_2$), thiosemicarbazides (—NH—C(S)—NH—NH), hydrazones (—N=NH), or hydrazides (—C(O)—NH—$NH_2$), especially $NH_2$; and Z is ribose or deoxyribose, preferably deoxyribose.

In another preferred embodiment, G is N; X is OH; Y is NHRQ, said R is a lower alkane; and Q is an amine, wherein said amine comprises $NH_2$, polyalkylaminos, aminoalkylamines, hydrazines (—NH—NH—), hydroxylamines (—NH—OH), semicarbazides (—NH—C(O)—NH—$NH_2$), thiosemicarbazides (—NH—C(S)—NH—$NH_2$), hydrazones (—N=NH), or hydrazides, especially $NH_2$; and Z is ribose or deoxyribose, preferably deoxyribose. In a more preferred embodiment, G is N; X is OH; Y is NHRQ, said R is hexane and Q is NH; and Z is ribose or deoxyribose, preferably deoxyribose.

In certain other preferred embodiments, Y is NHRQ, and the reactive functionality, Q, is a thiol group, aldehyde, ketone, alcohol, or an alkoxy group; and Z is ribose or deoxyribose, preferably deoxyribose. In other preferred embodiments, Y is RQ and the reactive functionality Q is a thiol group, aldehyde, ketone, alcohol, or an alkoxy group; and Z is ribose or deoxyribose, preferably deoxyribose.

Generally, sugar moieties may be attached to the novel purine based compounds of the invention using methods known in the art. See Revankar, supra.

Substituted sugars may be synthesized according to the methods disclosed in PCT Patent Application Number PCT\US91\00243 assigned to a common assignee hereof, entitled "Compositions and Methods for Detecting and Modulating RNA Activity and Gene Expression," the disclosures of which are incorporated herein by reference to disclose more fully such modifications.

For example, a substituted sugar as, methyl 3-O-(t-butyldiphenylsilyl)-2,5-dideoxy-5-C-formyl-α/β -D-erythropentofuranoside, can be prepared by modifying 2-deoxy-D-ribose to methyl 2-deoxy-α/β-D-erythro-pentofuranoside (prepared according to the method of Motawai et al., *Liebigs Ann. Chem.*, 1990, 599–602), which on selective tosylation followed by 3-O-silylation gave methyl 3-O-(t-butyldimethylsilyl)-2-deoxy-5-O-tosyl-α/β-D-erythro-pentofuranoside.

As will be appreciated by persons of ordinary skill in the art, variations in the structures of the sugar moieties useful in the preparation of the subject compositions may be made without deviating from the spirit of the invention. Suitable substituents on the sugar moiety include, but are not limited to, OH, lower alkyl, substituted lower alkyl, aralkyl, heteroalkyl, heterocycloalkyl, aminoalkylamino, heterocycloalkyl, polyalkylamino, substituted silyl, F, Cl, Br, CN, $CF_3$, $OCF_3$, OCN, O-alkyl, S-alkyl, SOMe, $SO_2Me$, $ONO_2$, $NO_2$, $N_3$, $NH_2$, NH-alkyl, $OCH_2CH=CH$, $OCH_2CCH$, OCCHO, or an RNA cleaving moiety. It is not necessary that every sugar linking function be in a modified form because a substantial number and even a predominance of the linking groups may exist in the native, phosphorodiester form as long as the overall targeting portion of the compositions of the invention exhibit an effective ability to penetrate into the intracellular spaces of cells of the organism in question or otherwise to contact the target RNA and to specifically bind therewith to form a hybrid capable of detecting and modulating RNA activity. Of course, fully unmodified, native phosphorodiester structure may also be used for those purposes.

In other preferred embodiments, Z will be a nitrogen protecting group. Generally, protecting groups are known per se as chemical functional groups that can be selectively appended to and removed from functionalities, such as amine groups. These groups are present in a chemical compound to render such functionality inert to chemical reaction conditions to which the compound is exposed. See, e.g., Greene, et al., Protective Groups in Organic Synthesis, (John Wiley & Sons, New York, 2d ed. 1991). Numerous amine protecting groups are known in the art, including, but not limited to, the allyloxycarbonyl (Alloc), benzyloxycarbonyl (CBz), chlorobenzyloxycarbonyl, t-butyloxycarbonyl (Boc), fluorenylmethoxycarbonyl (Fmoc), isonicotinyloxycarbonyl (i-Noc) groups. (see, e.g., Veber Hirschmann, et al., *J. Org. Chem.* 1977, 42, 3286 and Atherton, et al., (Academic Press, New York, Gross & Meinhofer, eds, 1983). For example, it is known that the Boc group can protect an amine group from base and from reducing conditions but that it can be removed with acid. Other nitrogen protecting groups will be apparent to those skilled in the art and may be used without detracting from the spirit of the invention. Any ester protecting groups known to those skilled in the art may be used; tetrahydropyranyl is an example of such a group. See Greene, supra.

The invention further provides compositions comprising a sugar and base moiety as discussed above, with the 3' position of the sugar moiety derivatized with a phosphate group. Generally, nucleotides of the invention may be prepared by protecting the 5' position of the sugar moiety of the imidazole ring and derivatizing the 3' position with an appropriate phosphoramidite or other phosphate suitable for use on a DNA synthesizer, including without limitation, alkyl phosphonates, phosphorothioates, or phosphorotriesters.

Generally, the compounds of the invention may be synthesized under the following reaction conditions. The following reaction describes attachment of the 3-(1H-imidazol-1-yl)propyl moiety to the 2-amino group of deoxyguanosine and 2-aminodeoxyadenosine, and subsequent incorporation of these novel nucleosides into oligo-nucleotides. The numbers enclosed in the parentheses refer to the compounds on the reaction scheme depicted below in the Examples section.

2-Chloro-9-(2-deoxy-β-D-erythropentofuranosyl)inosine (3), a versatile, key intermediate, was obtained by heating 2,6-dichloro-9-(2-deoxy-b-D-erythropentofuranosyl)purine (1), Kazimierczuk et al., *J. Am. Chem. Soc.* 1984, 106, 6379, with sodium hydride (NaH) in allyl alcohol, followed by hydrogenation of the intermediate (2) with Pd/C at atmospheric pressure. For similar procedure see Kern et al., *Heterocyclic Chem.*, 1980, 17, 461. Displacement of the 2-chloro atom of (3) with 1-(3-aminopropyl)imidazole gave (4). The isobutyryl derivative of (4), Lesnik, supra, was subjected to the Mitsunobu reaction condition, Himmelsbach et al., *Tetrahedron*, 1984, 40, 59, in the presence of 2-(p-nitrophenyl) ethanol to provide fully protected nucleoside (6). Selective removal of the isobutyryl groups in (6), followed by dimethoxy-tritylation, Schaller et al., *Am. Chem. Soc.*, 1963, 85, 3821 and phosphitylation, Karpyshev et al., *Russ. Chem. Rev.*, 1988, 57, 886 afforded the deoxyguanosine amidite synthon (8) in 73% yield.

2-Chloro-deoxyadenosine (9) Christensen, et al., *J. Med. Chem.* 1972, 15, 735 was treated with 1-(3-aminopropyl)imidazole to provide $N^2$-substituted 2-aminodeoxyadenosine (10) which was protected by sequential treatment with TipSiCl, Markiewicz, et al., *Nucleic. Acid Res., Symp. Ser.* 1980, 7, 115 and isobutyrylchloride (IbCl) to afford (12). Removal of the TipSi protecting group of (12) with $Bu_4NF$, Huss et al., *Org. Chem. Soc.*, 1988, 53, 499 and subsequent dimethoxytritylation and phosphitylation provided the deoxyadenosine amidite synthon (14).

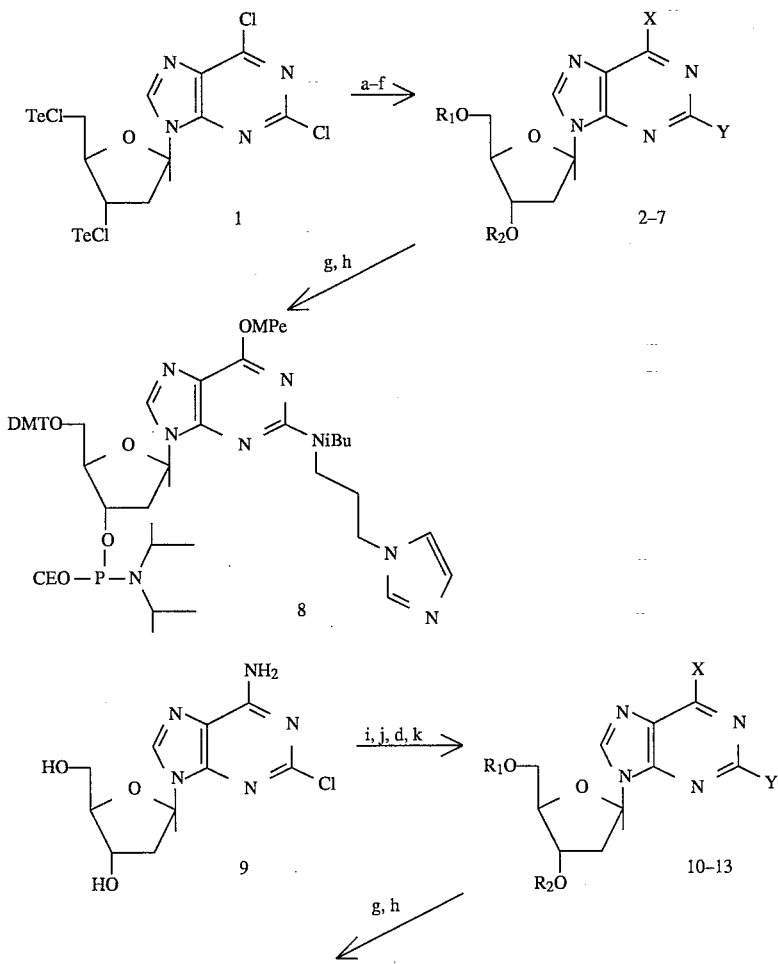

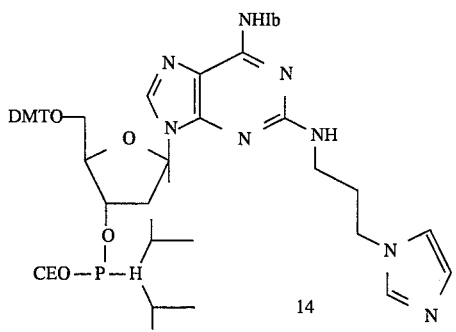

1. 2,6-Dichloro-9-(2'-deoxy-β-D-erythro-pentofuransyl)purine.
2. $R_1$ and $R_2$=H; X=Allyloxy; Y=Cl.
3. $R_1$ and $R_2$=H; X=OH; Y=Cl.
4. $R_1$ and $R_2$=H; X=OH; Y=NH(CH$_2$)$_3$Im.
5. $R_1$ and $R_2$=Ib; X=OH; Y=IbN(CH$_2$)$_3$Im.
6. $R_1$ and $R_2$=Isobutyryl; X=ONPE; Y=IbN(CH$_2$)$_3$Im.
7. $R_1$ and $R_2$=H; X=ONPE; Y=IbN(CH$_2$)$_3$Im.
8. Deoxyguanosine amidite synthon.
9. 2-Chloro-deoxyadenosine.
10. $R_1$ and $R_2$=H; X=NH$_2$; Y=NH(CH$_2$)$_3$—Im.
11. $R_1$ and $R_2$=TipSi; X=NH$_2$; Y=NH(CH$_2$)$_3$—Im.
12. $R_1$ and $R_2$=H; NHIb; Y=NH(CH$_2$)$_3$—Im.
13. $R_1$ and $R_2$=OH; X=NHIb; Y=NH(CH$_2$)$_3$—Im.
Ib=Isobutyryl
Im=Imidazole
NPE=(Nitrophenyl)ethanol
Reaction Conditions:
(a) NaH/Allyl alcohol; (b) Pd/C/H/EtOH; (c) 1-(3-Aminopropyl)imidazole/2-ethoxyethanol (90° C.); (d) IbCl/TEA/PY; (e) 2-(p-nitrophenyl)ethanol/Ph$_3$P/DEAD/Dioxane; (f) NH$_4$OH/CH$_3$OH; (g) DMTCl/TEA/PY; (h) 2-Cyanoethyl N,N-diisopropylchlorophosphoramidite/N,N-diisopropylethylamine/CH$_2$Cl$_2$; (i) 1-(3 -Aminopropyl)imidazole/2-Methoxyethanol (125° C.); (j) TipSiCl/TEA/PY; and (k) Bu$_4$NF/THF.

In another aspect of the invention, oligonucleotides or oligonucleotide analogs incorporating the novel compounds of the invention are provided. Generally, the oligonucleotides or oligonucleotide analogs may comprise a sugar modified or native oligonucleotide containing a target sequence that is specifically hybridizable with a preselected nucleotide sequence, a sequence of DNA or RNA that is involved in the production of proteins whose synthesis is ultimately to be modulated or inhibited in its entirety.

In certain preferred embodiments, the oligonucleotides of the invention comprise:

a first oligonucleotide region and a second nucleotide region;

together said first and said second region of a nucleotide sequence essentially complementary to at least a portion of said RNA;

said first region including at least one nucleotide having a base unit as defined above in connection with the heterocyclic compounds of the invention; and said second region including a plurality of consecutive phosphorothiocite linked nucleotides having a 2'-deoxy-erythro-pentofuranosyl sugar moiety. In certain preferred embodiments, the sugar moiety is ribose or deoxyribose and said phosphate is a methylphosphonate, phosphorothioate, phosphoramidite, phosphorotriester. In other preferred embodiments, the oligonucleotides of the invention further comprise a third region that includes at least one nucleotide having a base unit as defined above in connection with the heterocyclic compounds of the invention; wherein said second region is positioned in said oligonucleotide between said first and third regions.

Incorporation of amidites (i.e., 8 and 14 in the reaction scheme outlines depicted below in connection with the synthesis of the heterocycles of the invention) into oligonucleotide sequences can be accomplished via automated DNA synthesis protocol. (Standard protocol using an ABI 380B DNA synthesizer was modified by increasing the wait step after the pulse delivery of tetrazole to 900 seconds. Deprotection conditions are discussed in Himmelsbach, et al., *Tetrahedron*, 1984, 40, 59).

Generally, oligonucleotides or oligonucleotide analogs incorporating the novel compounds of the invention may be synthesized, conveniently through solid state synthesis of known methodology, to be complementary to or at least to be specifically hybridizable with the preselected nucleotide sequence of the RNA or DNA. Nucleic acid synthesizers are commercially available and their use is generally understood by persons of ordinary skill in the art as being effective in generating nearly any oligonucleotide or oligonucleotide analog of reasonable length which may be desired.

The resulting novel oligonucleotides or oligonucleotide analogs are synthesized by the standard solid phase, automated nucleic acid synthesizer such as the Applied Biosystems, Incorporated 380B or MilliGen/Biosearch 7500 or 8800. Triester, phosphoramidite, or hydrogen phosphonate coupling chemistries, *Oligonucleotides Antisense Inhibitors*, supra, pp. 7–24, are used in with these synthesizers to provide the desired oligonucleotides or oligonucleotide analogs. The Beaucage reagent, *J. Am. Chem. Society*, 1990, 112, 1253–1255 or elemental sulfur, Beaucage et al., *Tetrahedron Letters*, 1981, 22, 1859–1862, is used with phosphoramidite or hydrogen phosphonate chemistries to provide substituted phosphorothioate oligonucleotides. These oligonucleotide compositions comprise a targeting portion specifically hybridizable with a preselected nucleotide sequence of RNA, some of the phosphodiester bonds may be substituted with a structure that functions to enhance the compositions3 ability to penetrate into cells' intracellular region where the RNA, whose activity is to be modulated, is located. Standard backbone modifications include, but are not limited to, phosphorothioates, methyl phosphonates, phosphoramidites, and phosphorotriesters. These substitutions are thought in some cases to enhance the sugar modified oligonucleotides' properties. These phosphate bond modifications are disclosed as set forth in U.S. Patent Applications assigned to a common assignee hereof, entitled "Backbone Modified Oligonucleotide Analogs," Ser. No. 703,169 and "Heteroatomic Oligonucleotide Linkages," Ser. No. 903,160, the disclosures of which are incorporated herein by reference to disclose more fully such modifications. Backbone modifications may be used without departing from the spirit of the invention. It is not necessary, however, that the compounds of the invention have modified phosphate backbones.

Modifications that may provide oligonucleotides or oligonucleotide analogs that are substantially less ionic than native forms and facilitate penetration of modified or unmodified oligonucleotides into the intracellular spaces are also contemplated by this invention. Any of the existing or yet to be discovered methods for accomplishing this goal may be employed in accordance with the practice of the present invention. As will be appreciated by those skilled in the art, modifications of the phosphate bond find utility in this regard. Variations in the phosphate backbone useful in the preparation of the subject compositions may be made without deviating from the spirit of the invention. Modifications at the phosphorous atom are set forth in an U.S. Pat. No. 5,138,048, entitled "Polyamine Oligonucleotides to Enhance Cellular Uptake," and assigned to a common assignee hereof.

Although the invention is primarily directed to substitutions at the N-2 position of a purine base or heterocycle, other positions for attachment of reactive and non-reactive functionalities having a similar effect may be found, especially when further modifications of the purine structure are undertaken as may be done by persons of ordinary skill in the art without deviating from the spirit of the present invention. Once again, it is to be understood that preferably one, or at most a few RNA cleaving moieties are generally to be employed. Thus, artisans in the field will have great latitude in selecting means for attaching the RNA cleaving moieties, the pharmacodynamic improving groups, or the pharmacokinetic improving groups in accordance with this invention.

The present invention is further described in the following examples. These examples are for illustrative purposes only, and are not to be construed as limiting the appended claims.

EXAMPLES

Examples 1–45 are depicted in synthetic Scheme 1, which immediately follows Example 45. Examples 46–53 are depicted in synthetic Scheme 2, which immediately follows Example 53. Examples 54–56 are depicted in synthetic Scheme 3, which immediately follows Example 56. The numbers in parantheses following the Example's title compound correspond to the compound numbers on the respective schemes.

EXAMPLE 1

2,6-Dichloro-9-(2-deoxy-3,5-di-O-p-toluoyl-β-D-erythro-pentofuranosyl)purine. (1)

To a stirred solution of 2,6-dichloropurine (25.0 g, 132.27 mmol) in dry acetonitrile (1000 mL) was added sodium hydride (60% in oil, 5.40 g, 135 mmol) in small portions over a period of 30 minutes under argon atmosphere. After the addition of NaH, the reaction mixture was allowed to stir at room temperature for 30 minutes. Predried and powdered 1-chloro-2-deoxy-3,5,di-O-p-toluoyl-β-D-erythro-pentofuranose (53.0 g, 136 mmol) was added during a 15 minute period and the stirring continued for 10 hours at room temperature over argon atmosphere. The reaction mixture was evaporated to dryness and the residue dissolved in a mixture of $CH_2Cl_2/H_2O$ (250:100 mL) and extracted in dichloromethane (2×250 mL). The organic extract was washed with brine (100 mL), dried, and evaporated to dryness. The residue was dissolved in dichloromethane (300 mL), mixed with silica gel (60–100 mesh, 250 g) and evaporated to dryness. The dry silica gel was placed on top of a silica gel column (250–400 mesh, 12×60 cm) packed in hexane. The column was eluted with hexanes (1000 mL), toluene (2000 mL), and toluene:ethyl acetate (9:1, 3000 mL). The fractions having the required product were pooled together and evaporated to give 52 g (72%) of 3 as white solid. A small amount of solid was crystallized from ethanol for analytical purposes. mp 160°–162° C.; $^1$H NMR (DMSO-$d_6$); δ2.36 (s, 3H, $CH_3$), 2.38 (s, 3H, $CH_3$), 2.85 (m, 1H, $C_2$'H), 3.25 (m, 1H, $C_2$'H), 4.52 (m, 1H, $C_4$H), 4.62 (m, 2H, $C_5.CH_2$), 5.80 (m, 1H, $C_3$'H), 6.55 (t, 1H, $J_{1',2}$=6.20 Hz, $C_1.H$), 7.22 (dd, 2H, ArH), 7.35 (dd, 2H, ArH), 7.72 (dd, 2H, ArH), 7.92 (dd, 2H, ArH), and 8.92 (s, 1H, $C_8H$).

EXAMPLE 2

2-Chloro-6-allyloxy-9-(2'-deoxy-β-D-erythropentofuranosyl)purine. (2)

To a stirred suspension of 2,6-dichloro-9-(2'-deoxy-3',5'-di-O-p-toluoyl-β-D-erythro-pentofuranosyl)-purine (1, 10.3 g, 19.04 mmol) in allyl alcohol (150 mL) was added sodium hydride (60% 0.8 g, 20.00 mmol) in small portions over a 10 minute period at room temperature. After the addition of NaH, the reaction mixture was placed in a preheated oil bath at 55° C. The reaction mixture was stirred at 55° C. for 20 minutes with exclusion of moisture. The reaction mixture was cooled, filtered, and washed with allyl alcohol (50 mL). To the filtrate IRC-50 (weakly acidic) $H^+$ resin was added until the pH of the solution reached 4–5. The resin was filtered, washed with methanol (100 mL), and the filtrate was evaporated to dryness. The residue was absorbed on silica gel (10 g, 60–100 mesh) and evaporated to dryness. The dried silica gel was placed on top of a silica column (5×25 cm, 100–250 mesh) packed in dichloromethane. The column was then eluted with $CH_2Cl_2$/acetone (1:1). The fractions having the product were pooled together and evaporated to dryness to give 6 g (96%) of the title compound as foam. $^1$H NMR ($Me_2SO$-$d_6$) δ2.34 (m, 1H, $C_2.H$), 2.68 (m, 1H, $C_2.H$), 3.52 (m, 2H, $C_5.H$), 3.86 (m, 1H, $C_4.H$), 4.40 (m, 1H, $C_3.H$), 4.95 (t, 1H, $C_5.OH$), 5.08 (d, 2H, $CH_2$), 5.35 (m, 3H, $CH_2$ and $C_3.OH$), 6.10 (m, 1H, CH), 6.35 (t, 1H, $J_{1',2}$=6.20 Hz, $C_1.H$), 8.64 (s, 1H, $C_8H$). Anal. Calcd for $C_{13}H_{15}ClN_4O_4$: C, 47.78; H, 4.63; N, 17.15; Cl, 10.86. Found: C, 47.58; H, 4.53; N, 17.21; Cl, 10.91.

EXAMPLE 3

2-Chloro-9-(2'-deoxy-β-D-erythro-pentofuranosyl)inosine. (3)

A mixture of 2 (6 g, 18.4 mmol), Pd/C (10%, 1 g) and triethylamine (1.92 g, 19.00 mmol) in ethyl alcohol (200 mL) was hydrogenated at atmospheric pressure during 30 minute periods at room temperature. The reaction mixture was followed by the absorption of volume of hydrogen. The reaction mixture was filtered, washed with methanol (50 mL), and the filtrate evaporated to dryness. The product 5.26 g (100%) was found to be moisture sensitive and remained as a viscous oil. The oil was used as such for further reaction without purification. A small portion of the oil was dissolved in water and lyophilized to give an amorphous solid: $^1$H NMR ($Me_2SO$-$d_6$) δ 2.35 (m, 1H, $C_2.H$), 2.52 (m, 1H, $C_2.H$), 3.54 (m, 2H, $C_5.H$), 3.82 (m, 1H, $C_4.H$), 4.35 (m, 1H, $C_3.H$), 4.92 (b s, 1H, C$_5$·OH), 5.35 (s, 1H, C$_3$·OH), 6.23 (t, 1H, J$_{1',2'}$=6.20 Hz, C$_1$·H), 8.32 (s, 1H, C$_8$H), 13.36 (b s, 1H, NH).

EXAMPLE 4

N$_2$-[Imidazol-1-yl(propyl)]-9-(2'-deoxy-β-D-erythro-pentofuranosyl)guanosine. (4)

A solution of the nucleoside of 3 (10.3 g, 36.00 mmol) and 1-(3-aminopropyl)imidazole (9.0 g, 72.00 mmol) in 2-methoxyethanol (60 mL) was heated in a steel bomb at 100° C. (oil bath) for 24 hours. The bomb was cooled to 0° C., opened carefully and the precipitated solid was filtered. The solid was washed with methanol (50 mL), acetone (50 mL), and dried over sodium hydroxide to give 9 g (67%) of pure 4. A small amount was recrystallized from DMF for analytical purposes: mp 245°–47° C.: $^1$H NMR (Me$_2$SO-d$_6$) δ1.94 (m, 2H, CH$_2$), 2.20 (m, 1H, C$_2$·H), 2.54 (m, 1H, C$_2$·H), 3.22 (m, 2H, CH$_2$), 3.51 (m, 2H, C$_5$·H), 3.80 (m, 1H, C$_4$·H), 3.98 (m, 2H, CH$_2$), 4.34 (m, 1H, C$_3$·H), 4.90 (b s, 1H, C$_5$·OH), 5.51 (s, 1H, C$_3$·OH), 6.12 (t, 1H, J$_{1',2'}$=6.20 Hz, C$_1$·H), 6.46 (b s, 1H, NH), 6.91 (s, 1H, ImH), 7.18 (s, 1H, ImH), 7.66 (s, 1H, ImH), 7.91 (s, 1H, C$_8$H), 10.60 (b s, 1H, NH). Anal. Calcd for C$_{16}$H$_{21}$N$_7$O$_4$: C, 51.19; H, 5.64; N, 26.12. Found: C, 50.93; H, 5.47; N, 26.13.

EXAMPLE 5

3',5'-Di-O-isobutyryl-N$_2$-[imidazol-1-yl(propyl)]-N$_2$-isobutyryl-9-(2'-deoxy-β-D-erythro-pentofuranosyl)guanosine. (5)

To a well dried solution of the substrate of 4 (1.5 g, 4.00 mmol) and triethylamine (1.62 g, 16.00 mmol) in dry pyridine (30 mL) and dry DMF (30 mL) was added isobutyryl chloride (1.69 g, 16.00 mmol) at room temperature. The reaction mixture was allowed to stir at room temperature for 12 hours and evaporated to dryness. The residue was partitioned between dichloromethane (100 mL) and water (50 mL) and extracted with CH$_2$Cl$_2$ (2×200 mL). The organic extract was washed with brine (100 mL) and dried over anhydrous MgSO$_4$. The dried organic extract was evaporated to dryness and the residue was purified over flash chromatography using CH$_2$Cl$_2$/MeOH as eluent. The pure fractions were pooled, evaporated to dryness which on crystallization from CH$_2$Cl$_2$/MeOH gave 1.8 g (77%) of 5 as a colorless crystalline solid: mp 210°–212° C.; $^1$H NMR (Me$_2$SO-d$_6$) δ1.04 (m, 18H, 3 Isobutyryl CH$_3$), 1.94 (m, 2H, CH$_2$), 2.56 (m, 4H, C$_2$'H and 3 Isobutyryl CH) 2.98 (m, 1H, C$_2$'H), 3.68 (m, 2H, CH$_2$), 3.98 (m, 2H, CH$_2$), 4.21 (2 m, 3H, C$_5$·H and C$_4$·H), 5.39 (m, 1H, C$_3$·H), 6.30 (t, 1H, J$_{1',2'}$=6.20 Hz, C$_1$·H), 6.84 (s, 1H, ImH), 7.18 (s, 1H, ImH), 7.34 (s, 1H, ImH), 8.34 (s, 1H, C$_8$H), 10.60 (b s, 1H, NH). Anal. Calcd for C$_{28}$H$_{39}$N$_7$O$_7$: C, 57.42; H, 6.71; N, 16.74. Found: C, 57.29; H, 6.58; N, 16.56.

EXAMPLE 6

6-O-[2-(4-Nitrophenyl)ethyl]-N$_2$-3',5'-tri-O-isobutyryl-N$_2$-[imidazol-1-yl(propyl)]-9-(2'-deoxy-β-D-erythro-pentofuranosyl)guanosine. (6)

To a stirred solution of 5 (2.0 g, 3.42 mmol), triphenylphosphine (2.68 g, 10.26 mmol) and p-nitrophenyl ethanol (1.72 g, 10.26 mmol) in dry dioxane was added diethylazodicarboxylate (1.78 g, 10.26 mmol) at room temperature. The reaction mixture was stirred at room temperature for 12 hours and evaporated to dryness. The residue was purified by flash chromatography over silica gel using CH$_2$Cl$_2$/acetone as the eluent. The pure fractions were pooled together and evaporated to dryness to give 2.4 g (96%) of the title compound as an amorphous solid. $^1$H NMR (Me$_2$SO-d$_6$) δ1.04 (m, 18H, 3 Isobutyryl CH$_3$), 1.94 (m, 2H, CH$_2$), 2.50 (m, 3H, C$_2$·H and 2 Isobutyryl CH), 3.00 (m, 1H, C$_2$·H), 3.12 (m, 1H, Isobutyryl CH), 3.24 (m, 2H, CH$_2$), 3.82 (m, 2H, CH$_2$), 3.98 (m, 2H, CH$_2$), 4.21 (2 m, 3H, C$_5$·CH$_2$ and C$_4$·H), 4.74 (m, 2H, CH$_2$), 5.39 (m, 1H, C$_3$·H), 6.34 (t, 1H, J$_{1',2'}$=6.20 Hz, C$_1$·H), 6.82 (s, 1H, ImH), 7.08 (s, 1H, ImH), 7.56 (s, 1H, ImH), 7.62 (d, 2H, ArH), 8.1 (d, 2H, ArH), 8.52 (s, 1H, C$_8$H). Anal. Calcd for C$_{36}$H$_{46}$N$_8$O$_9$·1/2H$_2$O: C, 58.13; H, 6.37; N, 15.01. Found: C, 58.33; H, 6.39; N, 14.75.

EXAMPLE 7

6-O-[2-(4-Nitrophenyl)-ethyl]-N$_2$-isobutyryl-N$_2$-[imidazol-1-yl-(propyl)]-9-(2'-deoxy-β-D-erythro-pentofuranosyl)guanosine. (7)

To a stirred solution of 6 (9.00 g, 12.26 mmol) in methanol (250 ml) was treated with ammonium hydroxide (30%, 150 ml) at room temperature. The reaction mixture was stirred at room temperature for 4 hours and evaporated to dryness under reduced pressure. The residue was purified by flash chromatography over silica gel using CH$_2$Cl$_2$/MeOH as the eluent. The pure fractions were pooled together and evaporated to dryness to give 5.92 g (81%) of the title compound: $^1$H NMR (Me$_2$SO-d$_6$) δ1.04 (m, 6H, Isobutyryl CH$_3$), 1.96 (m, 2H, CH$_2$), 2.32 (m, 1H, C$_2$·H), 2.62 (m, 1H, C$_2$·H), 3.14 (m, 1H, Isobutyryl CH), 3.26 (m, 2H, CH$_2$), 3.52 (m, 2H, C$_5$·CH$_2$), 3.82 (m, 3H, CH$_2$ and C$_4$·H), 3.96 (m, 2H, CH$_2$), 4.36 (m, 1H, C$_3$·H), 4.70 (m, 2H, CH$_2$), 4.96 (b s, 1H, C$_5$·OH), 5.42 (b s, 1H, C$_3$·OH), 6.34 (t, 1H, J$_{1',2'}$=6.20 Hz, C$_1$·H), 6.82 (s, 1H, ImH), 7.12 (s, 1H, ImH), 7.54 (s, 1H, ImH), 7.62 (d, 2H, ArH), 8.16 (d, 2H, ArH), 8.56 (s, 1H, C$_8$H). Anal. Calcd for C$_{28}$H$_{34}$N$_8$O$_7$·1/2H$_2$O; C, 55.71; H, 5.84; N, 18.56. Found: C, 55.74; H, 5.67; N, 18.43.

EXAMPLE 8

5'-O-(4,4'-Dimethoxytrityl)-6-O-[2-(4-nitrophenyl)ethyl]-N$_2$-isobutyryl-N$_2$ -[imidazol-1-yl(propyl)]-2'-deoxy-β-D-erythro-pentofuranosyl)guanosine. (8)

The substrate 7 (5.94 g, 10 mmol), was dissolved in dry pyridine (75 mL) and evaporated to dryness. This was repeated three times to remove traces of moisture. To this well dried solution of the substrate in dry pyridine (100 mL) was added dry triethylamine (4.04 g, 40 mmol), 4-(dimethylamino)pyridine (1.2 g, 30 mmol) at room temperature. The reaction mixture was stirred at room temperature for 12 hours under argon atmosphere. Methanol (50 mL) was added and the stirring was continued for 15 minutes and evaporated to dryness. The residue was purified by flash chromatography over silica gel using dichloromethane-acetone containing 1% triethylamine as the eluent. The pure fractions were pooled together and evaporated to dryness to give 7.2 g (80%) of the title compound as a colorless foam: $^1$H NMR (Me$_2$SO-d$_6$) δ1.04 (m, 6H, Isobutyryl CH$_3$), 1.94 (m, 2H, CH$_2$), 2.34 (m, 1H, C$_2$·H), 2.80 (m, 1H, C$_2$·H), 3.04 (m, 1H, Isobutyryl CH), 3.18 (m, 2H, CH$_2$), 3.28 (m, 2H, CH$_2$), 3.62 (s, 3H, OCH$_3$), 3.66 (s, 3H, OCH$_3$), 3.74 (2 m, 2H, C$_5$·CH$_2$), 3.98 (m, 3H, CH$_2$ and C$_4$·H), 4.36 (m, 1H, C$_3$·H), 4.70 (m, 2H, CH$_2$), 5.44 (b s, 1H, C$_3$·OH), 6.32 (t, 1H, J$_{1',2'}$=6.20 Hz C$_1$·H), 6.64–7.32 (m, 15H, ImH and ArH), 7.52 (s, 1H, ImH), 7.62 (d, 2H, ArH), 8.16 (d, 2H, ArH), 8.42 (s, 1H, C$_8$H). Anal. Calcd for C$_{49}$H$_{52}$N$_8$O$_9$·H$_2$O: C, 64.32; H, 5.95; N, 12.25. Found: C, 64.23; H, 5.82; N, 12.60.

EXAMPLE 9

3'-O-(N,N-Diisopropylamino) (β-cyanoethoxy)phosphanyl]-5'-O-(4,4'-dimethoxytrityl)-6-O-[2-(4-nitrophenyl)ethyl]-N$_2$-isobutyryl-N$_2$-[imidazol-1 -yl(propyl)]-9-(2'-deoxy-β-D-erythro-pentofuranosyl)guanosine. (9)

The substrate of 8 (2.5 g, 2.7 mmol), was dissolved in dry pyridine (30 mL) and evaporated to dryness. This was repeated three times to remove last traces of water and dried over solid sodium hydroxide overnight. The dried 8 was dissolved in dry dichloromethane (30 mL) and cooled to 0° C. under argon atmosphere. To this cold stirred solution was added N,N-diisopropylethylamine (0.72 g, 5.6 mmol) followed by (β-cyanoethoxy)chloro(N,N-diisopropylamino) phosphate (1.32 g, 5.6 mmol) dropwise over a period of 15 minutes. The reaction mixture was stirred at 0° C. for 1 hour and at room temperature for 2 hours. The reaction mixture was diluted with dichloromethane (100 mL) and washed with brine (50 mL). The organic extract was dried over anhydrous $MgSO_4$ and the solvent was removed under reduced pressure. The residue was purified by flash chromatography over silica gel using hexane/acetone containing 1% triethylamine as the eluent. The main fractions were collected and evaporated to dryness. The residue was dissolved in dry dichloromethane (10 mL) and added dropwise, into a stirred solution of hexane (1500 mL), during 30 minutes. After the addition, the stirring was continued for an additional 1 hour at room temperature under argon. The precipitated solid was filtered, washed with hexane and dried over solid NaOH under vacuum overnight to give 2.0 g (65%) of the title compound as a colorless powder: $^1H$ NMR $(Me_2SO-d_6)$ δ1.04 (2 m, 18H, 3 Isobutyryl $CH_3$), 1.94 (m, 2H, $CH_2$), 2.44 (m 3H, $C_2.H$ and 2 Isobutyryl CH), 2.80 (m, 1H, $C_2.H$), 3.2 (m, 5H, 2 $CH_2$ and Isobutyryl CH), 3.44–3.98 (m, 12H, $CH_2$, $2OCH_3$ and $C_5.CH_2$), 4.16 (m, 1H, $C_4H$), 4.64 (m, 3H, $C_3.H$ and $CH_2$), 6.32 (t, 1H, $J_{1',2}$=6.20 Hz, $C_1.H$), 6.64–7.32 (m, 16H, 3 ImH and ArH), 7.44 (d, 2H, ArH), 8.16 (d, 3H, ArH and $C_8H$).

EXAMPLE 10

$N_2$-[Imidazol-1-yl(propyl)]-9-(2'-deoxy-β-D-erythro-pentofuranosyl)adenosine. (11)

A suspension of 2-chloro-9-(2'-deoxy-β-D-erythro-pentofuranosyl)adenosine (10, 10.68 g, 37.47 mmol) and 1-(3 aminopropyl)imidazole (12.5 g, 100 mmol) in 2-methoxyethanol (80 mL) was heated at 125° C. for 45 hours in a steel bomb. The bomb was cooled to 0° C., opened carefully, and evaporated to dryness. The residue was coevaporated several times with a mixture of ethanol and toluene. The residue was dissolved in ethanol which on cooling gave a precipitate. The precipitate was filtered and dried. The filtrate was evaporated to dryness and the residue carried over to the next reaction without further purification. $^1H$ NMR $(Me_2SO-d_6)$ δ1.94 (m, 2H, $CH_2$), 2.18 (m, 1H, $C_2.H$), 2.36 (m, 1H, $C_2.H$), 3.18 (m, 2H, $CH_2$), 3.52 (2 m, 2H, $C_5.CH_2$), 3.80 (m, 1H, $C_4H$), 4.02 (m, 2H, $CH_2$), 4.36 (m, 1H, $C_3.H$), 5.24 (b s, 2H, $C_3.OH$ and $C_5.OH$), 6.18 (t, 1H, $J_{1',2}$=6.20 Hz, $C_1.H$), 6.42 (t, 1H, NH), 6.70 (b s, 2H $NH_2$), 6.96 (s, 1H, ImH), 7.24 (s, 1H, ImH), 7.78 (s, 1H, ImH), 7.90 (s, 1H, $C_8H$). Anal. Calcd for $C_{16}H_{22}N_8O_3$: C, 51.33; H, 5.92; N, 29.93. Found: C, 51.30; H, 5.92; N, 29.91.

EXAMPLE 11

3',5'-O-[(Tetraisopropyldisiloxane-1,3-diyl)-$N_2$-(imidazol-1-yl)(propyl)]-9-(2'-deoxy-β-D-erythro-pentofuranosyl)aminoadenosine. (12)

The crude product 11 (14.03 g) was dissolved in dry DMF (100 mL) dry pyridine (50 mL), and evaporated to dryness. This was repeated three times to remove all the water. The dried substrate was dissolved in dry DMF (75 mL) and allowed to stir at room temperature under argon atmosphere. To this stirred solution was added dry triethylamine (10.1 g, 100 mmol) and 1,3-dichloro-1,1,3,3-tetraisopropyldisiloxane (TipSiCl, 15.75 g, 50.00 mmol) during a 15 minute period. After the addition of TipSiCl, the reaction mixture was allowed to stir at room temperature overnight. The reaction mixture was evaporated to dryness. The residue was mixed with toluene (100 mL) and evaporated again. The residue was purified by flash chromatography over silica gel using $CH_2Cl_2$/MeOH as eluent. The pure fractions were pooled and evaporated to dryness to give 12.5 g (54%) of 12 as an amorphous powder: $^1H$ NMR $(Me_2SO-d_6)$ δ1.00 (m, 28H), 1.92 (m, 2H, $CH_2$), 2.42 (m, 1H, $C_2.H$), 2.80 (m, 1H, $C_2.H$), 3.18 (m, 2H, $CH_2$), 3.84 (2 m, 3H, $C_5.CH_2$ and $C_4.H$), 4.00 (t, 2H, $CH_2$), 4.72 (m, 1H, $C_3.H$), 6.10 (m, 1H, $C_1.H$), 6.48 (t, 1H, NH), 6.74 (b s, 2H, $NH_2$), 6.88 (s, 1H, ImH), 7.18 (s, 1H, ImH), 7.64 (s, 1H, ImH), 7.82 (s, 1H, $C_8H$). Anal. Calcd for $C_{28}H_{50}N_8O_4Si_2$: C, 54.33; H, 8.14; N, 18.11. Found: C, 54.29; H, 8.09; N, 18.23.

EXAMPLE 12

3',5'-O-(Tetraisopropyldisiloxane-1,3-diyl)-$N_6$-isobutyryl-$N_2$-[(imidazol-1-yl)propyl]-9-(2'-deoxy-β-D-erythro-pentofuranosyl)adenosine. (13)

A solution of 12 (12.0 g, 19.42 mmol) in pyridine (100 mL) was allowed to stir at room temperature with triethylamine (10.1 g, 100 mmol) under argon atmosphere. To this stirred solution was added isobutyryl chloride (6.26 g, 60 mmol) dropwise during a 25 minute period. The reaction mixture was stirred under argon for 10 hours and evaporated to dryness. The residue was partitioned between dichloromethane/water and extracted with dichloromethane (2×150 mL). The organic extract was washed with brine (30 mL) and dried over anhydrous $MgSO_4$. The solvent was removed under reduced pressure and the residue was purified by flash chromatography over silica gel using $CH_2Cl_2$/acetone as the eluent to give the 13 as a foam: $^1H$ NMR $(Me_2SO-d_6)$ δ1.00 (m, 34H), 1.92 (m, 2H, $CH_2$), 2.42 (m, 1H, $C_2.H$), 2.92 (m, 2H, $C_2.H$ and Isobutyryl CH), 3.24 (m, 2H, $CH_2$), 3.86 (m, 3H, $C_5.CH_2$ and $C_4.H$), 4.40 (m, 2H, $CH_2$), 4.74 (m, 1H, $C_3.H$), 6.22 (m, 1H, $J_{1',2}$=6.20 Hz, $C_1.H$), 6.82 (t, 1H, NH), 6.92 (s, 1H, ImH), 7.18 (s, 1H, ImH), 7.60 (s, 1H, ImH), 8.12 (s, 1H, $C_8H$), 10.04 (b s, 1H, NH). Anal. Calcd for $C_{32}H_{54}N_8O_5Si_2$: C, 55.94; H, 7.92; N, 16.31. Found: C, 55.89; H, 7.82; N, 16.23.

EXAMPLE 13

3',5'-Di-O-isobutyryl-$N_2$-[imidazol-1-yl(propyl)]-$N_6$-isobutyryl-9-(2'-deoxy-β-D-erythro-pentofuranosyl)adenosine. (14)

The crude product 11 (9.2 g, 24.59 mmol) was coevaporated three times with dry DMF/pyridine (100:50 mL). The above dried residue was dissolved in dry DMF (100 mL) and dry pyridine (100 mL) and cooled to 0° C. To this cold stirred solution was added triethylamine (20.2 g, 200 mmol) followed by isobutyryl chloride (15.9 g, 150 mmol). After the addition of IbCl, the reaction mixture was allowed to stir at room temperature for 12 hours. The reaction mixture was evaporated to dryness. The residue was extracted with dichloromethane (2×200 mL), washed with 5% $NaHCO_3$ (50 mL) solution, water (50 mL), and brine (50 mL). The organic extract was dried over dry $MgSO_4$ and the solvent was removed under reduced pressure. The residue was purified by flash column using $CH_2Cl_2$/acetone (7:3) as the eluent. The pure fractions were collected together and evaporated to give 7.0 g (44%) of 14 as a foam: $^1H$ NMR $(Me_2SO-d_6)$ δ1.00 (m, 18H, 3 Isobutyryl $CH_3$), 1.98 (m, 2H, $CH_2$), 2.42 (m, 3H, $C_2.H$ and 2 Isobutyryl CH), 2.92 (m, 2H, $C_2$H and Isobutyryl CH), 3.24 (m, 2H, $CH_2$), 4.04 (m, 2H, $CH_2$), 4.22 (m, 3H, $C_5$·$CH_2$ and $C_4$·H), 5.42 (m, 1H $C_3$·H), 6.24 (t, 1H, $J_{1',2'}$=6.20 Hz, $C_1$·H), 7.04 (s, 1H, ImH), 7.12 (t, 1H, NH), 7.32 (s, 1H, ImH), 8.00 (s, 1H, ImH), 8.12 (s, 1H, $C_8$H), 10.14 (b s, 1H, NH). Anal. Calcd for $C_{28}H_{40}N_8O_6$: C, 57.52; H, 6.89; N, 19.17. Found: C, 57.49; H, 6.81: N, 19.09.

EXAMPLE 14

$N_2$-Isobutyryl-$N_2$-[imidazol-1-yl(propyl)]-9-(2'-deoxy-β-D-erythro-pentofuranosyl)adenosine. (15)

Method 1: To a stirred solution of 13 (2.6 g, 3.43 mmol) in dry tetrahydrofuran (60 mL) was added tetrabutylammonium fluoride (1M solution in THF, 17.15 mL, 17.15 mmol) at room temperature. The reaction mixture was stirred at room temperature for 1 hour and quenched with $H^+$ resin. The resin was filtered, and washed with pyridine (20 mL) and methanol (50 mL). The filtrate was evaporated to dryness and the residue on purification over silica column using $CH_2Cl_2$/MeOH (95:5) gave the title compound in 59% (1 g) yield: $^1$H NMR ($Me_2SO$-$d_6$) δ1.04 (m, 6H, Isobutyryl $CH_3$), 1.98 (m, 2H, $CH_2$), 2.22 (m, 1H, Isobutyryl CH), 2.70 (m, 1H, $C_2$·H), 2.98 (m, 1H, $C_2$·H), 3.22 (m, 2H $CH_2$), 3.52 (2 m, 2H, $C_5$·$CH_2$), 3.82 (m, 1H, $C_4$·H), 4.04 (m, 2H, $CH_2$), 4.38 (m, 1H, $C_3$·H), 4.92 (b s, 1H, OH), 5.42 (b s, 1H, OH) 6.22 (t, 1H, $J_{1',2'}$=6.20 Hz, $C_1$·H), 6.92 (s, 1H, ImH), 7.06 (t, 1H, NH), 7.24 (s, 1H, ImH), 7.74 (s, 1H, ImH), 8.12 (s, 1H, $C_8$H), 10.08 (b s, 1H, NH). Anal. Calcd for $C_{20}H_{28}N_8O_4$·$H_2O$; C, 54.04; H, 6.35; N, 25.21. Found: C, 54.14; H, 6.53; N, 25.06.

Method 2: To an ice cold (0° to −5° C.) solution of 14 (7.4 g. 12.65 mmol) in pyridine:EtOH:$H_2O$ (70:50:10 mL) was added 1N KOH solution (0° C., 25 mL, 25 mmol) at once. After 10 minutes of stirring, the reaction was quenched with $H^+$ resin (pyridinium form) to pH 7. The resin was filtered, and washed with pyridine (25 mL) and methanol (100 mL). The filtrate was evaporated to dryness and the residue was purified by flash chromatography over silica gel using $CH_2Cl_2$/MeOH (9:1) as eluent. The pure fractions were pooled together and evaporated to give 1.8 g (37%) of 15.

EXAMPLE 15

5'-O-(4,4'-Dimethoxytrityl)-$N_6$-isobutyryl-$N_2$-[imidazol-1-yl(propyl)]-9-(2'-deoxy-β-D-erythro-pentofuranosyl)adenosine. (16)

To a well dried (coevaporated three times with dry pyridine before use) solution of 15 (3.6 g, 8.11 mmol) in dry pyridine (100 mL) was added triethylamine (1.01 g, 10.00 mmol) followed by 4,4'-dimethoxytrityl chloride (3.38 g, 10.00 mmol) at room temperature. The reaction mixture was stirred under argon for 10 hours and quenched with methanol (20 mL). After stirring for 10 minutes, the solvent was removed under reduced pressure. The residue was dissolved in dichloromethane (250 mL), washed with water (50 mL), and brine (50 mL), and dried over $MgSO_4$. The dried organic extract was evaporated to dryness to an orange foam. The foam was purified by flash chromatography over silica gel using $CH_2Cl_2$/MeOH (95:5) as eluent. The required fractions were collected together and evaporated to give 4.6 g (76%) of 16 as amorphous solid: $^1$H NMR ($Me_2SO$-$d_6$) δ1.04 (m, 6H, Isobutyryl $CH_3$), 1.90 (m, 2H, $CH_2$), 2.30 (m, 1H, $C_2$·H), 2.82 (m, 1H, $C_2$·H), 2.94 (m, 1H, Isobutyryl CH), 3.14 (m, 4H, $CH_2$ and $C_5$·$CH_2$), 3.72 (m, 6H, $OCH_3$), 3.92 (m, 3H, $CH_2$ and $C_4$·H), 4.44 (m, 1H, $C_3$·H), 5.44 (b s, 1H, $C_5$·OH), 6.28 (t, 1H, $J_{1',2'}$=6.20 Hz, $C_1$·H), 6.72–7.32 (m, 18H, ImH, NH and ArH), 7.64 (s, 1H ImH), 8.02 (s, 1H, $C_8$H), 10.10 (b s, 1H, NH). Anal. Calcd for $C_{41}H_{46}N_8O_6$: C, 65.93; H, 6.21; N, 15.00. Found: C, 65.81; H, 6.26; N, 14.71.

EXAMPLE 16

3'-O-[(N,N-diisopropylamino)(β-cyanoethoxy)phosphanyl]-5'-O-(4,4'-dimethoxytrityl)-$N_6$-isobutyryl-$N_2$-[imidazol-1-yl(propyl)]-9-(2'-deoxy-β-D-erythro-pentofuranosyl)adenosine. (17)

The substrate 16 (4.2 g, 5.6 mmol) was coevaporated with dry pyridine (50 mL) three times. The resulting residue was dissolved in dry dichloromethane (50 mL) and cooled to 0° C. in a ice bath. To this cold stirred solution was added N,N-diisopropylethylamine (1.44 g, 11.2 mmol) followed by (β-cyanoethoxy)chloro (N,N-diisopropylamino)phosphane (1.32 g, 5.6 mmol) over a period of 15 minutes. After the addition, the reaction mixture was stirred at 0° C. for 1 hour and room temperature for 2 hours. The reaction was diluted with dichloromethane (150 mL) and washed with 5% $NaHCO_3$ solution (25 mL) and brine (25 mL). The organic extract was dried over $MgSO_4$ and the solvent was removed under reduced pressure. The residue was purified by flash chromatography over silica gel using $CH_2Cl_2$/MeOH (98:2) containing 1% triethylamine as eluent. The pure fractions were collected together and evaporated to dryness to give 3.9 g (73%) of 17.

EXAMPLE 17

$N_2$-[Imidazol-4-yl(ethyl)]-9-(2'-deoxy-β-D-erythro-pentofuranosyl)guanosine. (18)

A mixture of 3 and histamine (4.4 g, 40.00 mmol) in 2-methoxyethanol (60 mL) was heated at 110° C. in a steel bomb for 12 hours. The steel bomb was cooled to 0° C., opened carefully, and the precipitated solid was filtered, washed with acetone and dried. The dried material was recrystallized from DMF/$H_2O$ for analytical purposes. Yield 6 g (79%): mp 220°–22° C.: $^1$H NMR ($Me_2SO$-$d_6$) δ2.22 (m, 1H, $C_2$·H), 2.64 (m, 1H, $C_2$·H), 2.80 (m, 1H, $CH_2$), 3.52 (m, 4H, $CH_2$ and $C_5$·$CH_2$), 3.80 (m, 1H, $C_4$·H), 4.42 (m, 1H, $C_3$·H), 4.98 (b s, 1H, $C_5$·OH), 5.44 (b s, 1H, $C_3$·OH), 6.16 (t, 1H, $J_{1',2'}$=6.20 Hz, $C_1$·H), 6.44 (b s, 1H, NH), 6.84 (s, 1H, ImH), 7.56 (s, 1H, ImH), 7.92 (s, 1H, $C_8$H), 10.60 (b s, 1H, NH), 11.90 (b s, 1H, NH). Anal. Calcd for $C_{15}H_{19}N_7O_4$: C, 49.85; H, 5.30; N, 27.13. Found: C, 49.61; H, 5.21; N, 26.84.

EXAMPLE 18

3',5'-O-(Tetraisopropyldisiloxane-1,3-diyl)-$N_2$-(imidazol-4-yl(ethyl)-9-(2'-deoxy-β-D-erythro-pentofuranosyl)guanosine. (19)

To a stirred suspension of 18 (2.4 g, 6.65 mmol) in dry DMF (50 mL) and dry pyridine (20 mL) was added triethylamine (4.04 g, 40.00 mmol) followed by 1,3-dichloro-1,1,3,3-tetraisopropyldisiloxane (4.18 g, 13.3 mmol) at room temperature. After the addition of TipSiCl, the reaction mixture was stirred overnight and evaporated to dryness. The residue was purified by flash chromatography over silica gel using $CH_2Cl_2$/MeOH (9:1) as eluent. The pure fractions were pooled together and evaporated to dryness to give 3.2 g (80%) of 19. The pure product was crystallized from acetone/dichloromethane as colorless solid. mp 245°–247° C.: $^1$H NMR ($Me_2SO$-$d_6$) δ1.00 (m, 28H), 2.46 (m, 1H, $C_2$·H), 2.72 (m, 1H, $C_2$·H), 2.84 (m, 1H, $CH_2$), 3.54 (m, 2H, $CH_2$), 3.90 (m, 3H, $C_4$·H and $C_5$·$CH_2$), 4.70 (m, 1H, $C_3$·H), 6.12 (t, 1H, $J_{1',2'}$=6.20 Hz, $C_1$·H), 6.68 (b s, 1H, NH), 7.20 (s, 1H, ImH), 7.80 (s, 1H, ImH), 8.40 (s, 1H, $C_8$H), 10.72 (b s, 1H, NH). Anal. Calcd for $C_{27}H_{45}N_7O_5Si_2$: C, 53.70; H, 7.51; N, 16.24. Found: C, 53.38; H, 7.63; N, 15.86.

EXAMPLE 19

3',5'-O-(Tetraisopropyldisiloxane-1,3-diyl)-6-O-diphenylcarbamoyl-$N_2$-[($N_2$-diphenylcarbamoyl)imidazol-4-yl(ethyl)]-9-(2'-deoxy-β-D-erythro-pentofuranosyl)guanosine. (20)

To a well stirred solution of the substrate 19 (6.03 g, 10.00 mmol) in dry DMF (50 mL) and dry pyridine (50 mL) was added N,N-diisopropylethylamine (5.16 g, 40.00 mmol) followed by diphenylcarbamoyl chloride (6.93 g, 30.00 mmol) at room temperature. The reaction mixture was allowed to stir at room temperature for 5 hours and evaporated to dryness. The residue was dissolved in $CH_2Cl_2$ (400 mL), washed with water (100 mL) and brine (50 mL), dried over $MgSO_4$, and evaporated to dryness. The residue was purified by flash chromatography using hexane/acetone (8:2) to give the title compound in 78.5% (7.8 g) yield: $^1$H NMR ($Me_2SO$-$d_6$) δ1.04 (m,28H), 2.54 (m, 1H, $C_2$·H), 2.65 (m, 1H, $C_2$·H), 2.72 (m, 2H, $CH_2$), 3.64 (m, 2H, $CH_2$), 3.86 (m, 1H, $C_4$·H), 4.00 (m, 2H, $C_5$·$CH_2$), 4.74 (m, 1H, $C_3$·H), 5.30 (b s, 1H, NH), 6.22 (m, 1H, $C_1$·H), 6.72 (s, 1H, ImH), 7.12–7.50 (m, 20H, ArH), 7.70 (s, 1H, ImH), 7.86 (s, 1H, $C_8$H). Anal. Calcd for $C_{53}H_{63}N_9O_7Si_2$: C, 64.02; H, 6.39; N, 12.68. Found: C, 64.13; H, 6.43; N, 12.79.

EXAMPLE 20

6-O-Diphenylcarbamoyl-$N_2$-[($N_1$-diphenylcarbamoyl)imidazol-4-yl(ethyl)]-9-(2'-deoxy-β-D-erythro-pentofuranosyl)guanosine. (21)

To a stirred solution of the protected derivative of 20 (1.8 g, 1.81 mmol) in pyridine/THF (30:20 mL) was added a 0.5M tetrabutyl-ammonium fluoride [prepared in a mixture of tetrahydrofuran-pyridine-water (8:1:1;v/v/v; 20 mL)] at room temperature. The reaction mixture was stirred for 15 minutes and quenched with H$^+$ resin (pydinium form) to pH 6–7. The resin was filtered off, and washed with pyridine (25 mL) and methanol (30 mL). The filtrate was evaporated to dryness and the residue was purified by flash chromatography using $CH_2Cl_2$/MeOH (95:5) to give 1.2 g (88%) of 21 as a colorless amorphous solid: $^1$H NMR ($Me_2SO$-$d_6$) δ2.32 (m, 1H, $C_2$·H), 2.72 (m, 2H, $CH_2$), 2.94 (m, 1H, $C_2$·H), 3.46 (m, 1H, $C_4$·H), 3.54–3.88 (m, 4H, $CH_2$ and $C_5$·$CH_2$), 4.00 (b s, 1H, $C_3$·H), 5.20 (b s, 2H, OH), 5.42 (t, 1H, NH), 6.10 (t, 1H, $J_{1',2}$=6.20 Hz $C_1$·H), 6.80 (s, 1H, ImH), 7.14–7.48 (m, 20H, ArH), 7.64 (s, 1H, ImH), 7.74 (s, 1H, $C_8$H). Anal. Calcd for $C_{41}H_{37}N_9O_6$: C, 65.50; H, 4.96; N, 16.77. Found: C, 65.31; H, 5.10; N, 16.40.

EXAMPLE 21

5'-O-(4,4'-Dimethoxytrityl)-6-diphenylcarbamoyl-$N_2$-[($N_2$-diphenylcarbamoyl)imidazol-4-yl(ethyl)]-9-(2'-deoxy-β-D-erythro-pentofuranosyl)guanosine. (22)

To a well dried solution of the substrate 21 (1.4 g, 1.87 mmol) in dry pyridine (70 mL) was added triethylamine (0.30 g, 3.0 mmol) followed by 4,4'-dimethoxytrityl chloride (0.85 g, 2.5 mmol) at room temperature. The stirring was continued overnight under argon atmosphere. Methanol (10 mL) was added, stirred for 10 minutes and evaporated to dryness. The residue was dissolved in $CH_2Cl_2$ (150 mL), washed with water (20 mL) and brine (20 mL), dried over $MgSO_4$, and the solvent removed under reduced pressure. The crude product was purified by flash chromatography over silica gel using $CH_2Cl_2$/acetone (7:3) containing 1% triethylamine as eluent. Yield 1.4 g (71%): $^1$H NMR ($Me_2SO$-$d_6$) δ2.44 (m, 1H, $C_2$·H), 2.62 (m, 2H, $CH_2$), 2.98 (m, 1H, $C_2$·H), 3.26 (m, 4H, $CH_2$ and $C_5$·$CH_2$), 3.40 (m, 1H, $C_4$·H), 3.68 (2 s, 6H, 2H $OCH_3$), 4.00 (m, 1H, $C_3$·H), 5.34 (t, 1H, NH), 5.44 (b s, 1H, $C_3$·OH), 6.12 (m, 1H, $C_1$·H), 6.66–7.48 (m, 34H, ImH and ArH), 7.62 (s, 1H, ImH), 7.78 (s, 1H, $C_8$H). Anal. Calcd for $C_{62}H_{55}N_9O_{84}$: C, 70.64; H, 5.26; N, 11.96. Found: C, 70.24; H, 5.39; N, 11.66.

EXAMPLE 22

3'-O-[(N,N-Diisopropylamino)(β-cyanoethoxy)phosphanyl]-5'-O-(4,4'-dimethoxytrityl)-6-0-diphenylcarbamoyl-$N_2$-[($N_1$-diphenylcarbamoyl)imidazol-4-yl(ethyl)]-9-(2'-deoxy-β-D-erythro-pentofuranosyl)guanosine. (23)

Well dried 22 was dissolved in dry dichloromethane (30 mL) and cooled to 0° C. under argon atmosphere. To this cold stirred solution was added N,N-diisopropylethylamine (0.39 g, 3.00 mmol) followed by (β-cyanoethoxy)chloro(N,N-diisopropylamino)phosphane (0.71 g, 3.0 mmol) over a period of 10 minutes. The reaction mixture was allowed to stir at room temperature for 2 hours and diluted with $CH_2Cl_2$ (120 mL). The organic layer was washed with 5% $NaHCO_3$ (25 mL), water (25 mL), and brine (25 mL). The extract was dried over anhydrous $MgSO_4$ and evaporated to dryness. The residue was purified by flash using hexane/ethyl acetate (3:7) containing 1% triethylamine as eluent. The pure fractions were pooled together and concentrated to dryness to give 1.0 g (70%) of 23 as a foam: $^1$H NMR ($Me_2SO$-$d_6$) δ1.12 (m, 12H, 2 Isobutyryl $CH_3$), 2.52 (m, 5H, $C_2$·H, $CH_2$ and Isobutyryl CH), 2.62 (m, 2H), 3.06 (m, 1H, $C_2$·H), 3.24 (m, 2H, $CH_2$) 3.40 (m, 2H, $CH_2$), 3.50–3.80 (m, 10H, 2$OCH_3$, $CH_2$ and $C_5$·$CH_2$), 4.08 (m, 1H, $C_4$·H), 4.82 (m, 1H, $C_3$·H), 5.74 (b s, 1H, NH), 6.24 (m, 1H, $C_1$·H), 6.64–7.52 (m, 34H, ImH and ArH), 7.62 (s, 1H, ImH), 7.94 (s, 1H, $C_8$H).

EXAMPLE 23

$N_2$-Nonyl-9-(2'-deoxy-β-D-erythro-pentofuranosyl)guanosine. (24)

A mixture of 2-chloro-2'-deoxyinosine and compound 3 (9.5 g, 33.22 mmol) and nonylamine (9.58 g, 67.00 mmol) in 2-methoxyethanol (60 mL) was heated at 120° C. for 12 hours in a steel bomb. The steel bomb was cooled to 0° C., opened carefully and the solvent removed under reduced pressure. The residue was coevaporated with a mixture of dry pyridine/dry toluene (50 mL each). The above process was repeated for three times and the resultant residue was carried over to the next reaction without further purification. A small amount of material was precipitated from the solution which was filtered and dried: mp 164°–167° C: $^1$H NMR ($Me_2SO$-$d_6$) δ0.82 (t, 3H, $CH_3$), 1.24 (m, 12H, 6 $CH_2$), 1.48 (m, 2H, $CH_2$), 2.18 (m, 1H, $C_2$·H), 2.62 (m, 1H, $C_2$·H), 3.22 (m, 2H, $CH_2$), 3.50 (m, 2H, $C_5$·$CH_2$), 3.78 (m, 1H, $C_4$·H), 4.32 (m, 1H, $C_3$·H), 4.84 (t, 1H, $C_5$·OH), 5.24 (m, 1H, $C_3$·OH), 6.12 (m, 1H, $C_1$·H), 6.44 (b s, 1H, NH), 7.86 (s, 1H, $C_8$H), 10.52 (b s, 1H, NH). Anal. Calcd for $C_{19}H_{31}N_5O_4$·$H_2O$: C, 55.45; H, 8.08; N, 17.00. Found: C, 55.96; H, 7.87; N, 16.59.

EXAMPLE 24

3',5'-Tri-O-isobutyryl-$N_2$-isobutyryl-$N_2$nonyl-9-(2'-deoxy-β-D-erythro-pentofuranosyl)guanosine. (25)

The crude product of 24 (18 g, 32.91 mmol) was coevaporated three times with a mixture of dry DMF/pyridine (50 mL each). The residue was dissolved in dry pyridine (150 mL) and cooled to 0° C. To this cold stirred solution was added triethylamine (30.3 g, 300 mmol) followed by isobutyryl chloride (21.2 g, 200 mmol) over a 30 minute period. After the addition of IbCl, the reaction mixture was allowed to stir at room temperature for 10 hours and was then evaporated to dryness. The residue was partitioned between $CH_2Cl_2$/water (300:150 mL) and extracted in $CH_2Cl_2$. The organic extract was washed with 5% $NaHCO_3$ (50 mL), water (50 mL) and brine (50 mL), dried over anhydrous $MgSO_4$, and evaporated to dryness. The residue was purified by flash chromatography over silica gel using $CH_2Cl_2$/EtOAc (6:4) as eluent. The pure fractions were pooled and evaporated to give 10 g (40%) of 25 as foam: $^1H$ NMR ($Me_2SO$-$d_6$) δ0.82 (t, 3H, $CH_3$), 1.12 (m, 30H, 3 Isobutryl $CH_3$ and 6 $CH_2$), 1.44 (m, 2H, $CH_2$), 2.54 (m, 4H, $C_2$·H and 3 Isobutyryl CH), 3.00 (m, 1H, $C_2$·H), 3.62 (m, 2H, $CH_2$), 4.20 (m, 3H, $C_5$·$CH_2$ and $C_4$·H), 5.32 (m, 1H, $C_3$·H), 6.24 (t, 1H, $J_{1',2'}$=6.20 Hz, $C_1$·H), 8.28 (s, 1H, $C_8$H), 12.82 (b s, 1H, NH). Anal. Calcd for $C_{31}H_{49}N_5O_7$: C, 61.67; H, 8.18; N, 11.60. Found: C, 61.59. H, 8.23; N, 11.34.

EXAMPLE 25

3',5'-O-(Tetraisopropyldisiloxane-1,3-diyl)-$N_2$-nonyl-9-(2'-deoxy-β-D-erythro-pentofuranosyl)guanosine. (26)

To a well dried solution of the crude product of 24 (16.4 g, 30.00 mmol) in dry DMF (100 mL) and dry pyridine (100 mL) was added triethylamine (10.1 g, 100 mmol) and 1,3-dichloro-1,1,3,3-tetraisopropyldisiloxane (15.75 g, 50 mmol) during 30 min period. The reaction mixture was allowed to stir at room temperature overnight and was then evaporated to dryness. The crude product was dissolved in $CH_2Cl_2$ (300 mL), washed with water (100 mL), and brine (50 mL). The extract was dried over $MgSO_4$ and the solvent was removed under reduced pressure. The residue was purified over silica column using $CH_2C_2$/acetone (7:3) to give 14 g (59%) of 26 as colorless foam. This on crystallization with the same solvent provided crystalline solid. mp 210°–212° C.: $^1H$ NMR ($Me_2SO$-$d_6$) δ0.82 (m, 3H, $CH_3$), 1.02 (m, 28 H), 1.24 (m, 12H, 6 $CH_2$), 1.50 (m, 2H, $CH_2$), 2.42 (m, 1H, $C_2$·H), 2.84 (m, 1H, $C_2$·H), 3.24 (m, 2H, $CH_2$), 3.82 (m, 2H, $C_5$·$CH_2$), 3.92 (m, 1H, $C_4$·H), 4.72 (m, 1H, $C_3$·H), 6.12 (t, 1H, $J_{1',2'}$=6.20 Hz, $C_1$·H), 6.36 (b s, 1H, NH), 7.78 (s, 1H, $C_8$H), 10.38 (b s, 1H, NH). Anal. Calcd for $C_{31}H_{57}N_5O_5Si_2$: C, 58.54; H, 9.03; N, 11.01. Found: C, 58.64; H, 9.09; N, 10.89.

EXAMPLE 26

$N_2$-Isobutyryl-3',5'-O-(tetraisopropyldisiloxane-1,3-diyl)-$N_2$-nonyl-9-(2'-deoxy-β-D-erythro-pentofuranosyl)guanosine. (27)

To a solution of 26 (14.0 g, 17.72 mmol) in dry DMF (50 mL) and dry pyridine (150 mL) was added triethylamine (3.54 g, 35.00 mmol) and isobutyryl chloride (3.71 g, 3.5retool). The reaction mixture was stirred at room temperature overnight and evaporated to dryness. The residue was dissolved in $CH_2Cl_2$(250 mL), washed with 5% $NaHCO_3$ (50 mL), water (50 mL) and brine (50 mL), dried over $MgSO_4$, and the solvent removed under reduced pressure. The residue was purified by flash chromatography over silica gel using $CH_2Cl_2$/acetone (9:1) as eluent. The pure fractions were pooled together and evaporated to dryness to give 12.0 g (77%) of the title compound as foam: $^1H$ NMR ($Me_2SO$-$d_6$) δ0.80 (m, 3H, $CH_3$), 0.98 (m, 34H), 1.20 (m, 12H, 6 $CH_2$), 1.42 (m, 2H, $CH_2$), 2.52 (m, 2H, $C_2$·H and Isobutyryl CH), 2.82 (m, 1H, $C_2$·H), 3.62 (m, 2H, $CH_2$), 3.84 (m, 3H, $C_5$·$CH_2$ and $C_4$·H), 4.72 (m, 1H, $C_3$·H), 6.22 (t, 1H, $J_{1',2'}$=6.20 Hz, $C_1$·H), 8.18 (s, 1H, $C_8$H), 12.80 (b s, 1H, NH).

EXAMPLE 27

$N_2$-Isobutyryl-$N_2$-nonyl-9-(2'-deoxy-β-D-erythro-pentofuranosyl)guanosine. (28)

Method 1; The substrate of 25 (5.00 g, 6.6 mmol) was dissolved in methanol (100 mL) and treated with concentrated $NH_4OH$ (100 mL). The reaction mixture was stirred for 4 hours at room temperature and evaporated to dryness. The residue was purified by flash chromatography over silica gel using $CH_2Cl_2$/MeOH (95:5) as eluent. The required fractions were collected together and evaporated to dryness and the residue on crystallization from $CH_2Cl_2$/acetone gave a colorless crystalline solid. yield 2 g (66%): mp 113°–115° C.

Method 2: A stirred solution of 27 (4.29 g, 4.99 mmol) in dry tetrahydrofuran (50 mL) was treated with 1M solution of tetrabutylammonium fluoride (20 mL, 20.00 mmol). The reaction mixture was stirred at room temperature for 4 hours and evaporated to dryness. The residue was purified by flash chromatography using $CH_2Cl_2$/MeOH (95:5) to give 1.59 g (69%) of 28: $^1H$ NMR ($Me_2SO$-$d_6$) δ0.80 (m, 3H, $CH_3$), 0.98 (m, 6H, Isobutyryl $CH_3$), 1.16 (m, 12H, 6 $CH_2$), 1.42 (m, 2H, $CH_2$), 2.24 (m, 1H, $C_2$·H), 2.52 (m, 2H, $C_2$·H and Isobutyryl CH), 3.50 (m, 2H, $C_5$·$CH_2$), 3.62 (m, 2H, $CH_2$), 3.82 (m, 1H, $C_4$·H), 4.36 (m, 1H, $C_3$·H), 4.94 (t, 1H, $C_5$·OH), 5.34 (m, 1H, $C_3$·OH), 6.22 (t, 1H, $J_{1',2'}$=6.20 Hz, $C_1$·H), 8.28 (s, 1H, $C_8$H), 12.78 (b s, 1H, NH). Anal. Calcd for $C_{23}H_{37}N_5O_5$: C, 59.59; H, 8.05; N, 15.11. Found: C, 59.50; H, 8.08; N, 15.06.

EXAMPLE 28

5'-O-(4,4'-Dimethoxytrityl)-$N_2$-isobutyryl-$N_2$-nonyl-9-(2'-deoxy-β-D-erythro-pentofuranosyl)guanosine. (29)

To a stirred solution of 28 (2.00 g, 4.32 mmol) in dry pyridine (75 mL) was added triethylamine (0.61 g, 6.00 mmol) and 4,4'-dimethoxytrityl chloride (2.03 g, 6.00 mmol) at room temperature. The reaction was stirred under argon atmosphere for 6 hours and quenched with methanol (10 mL). The solvent was removed under reduced pressure and the residue dissolved in $CH_2Cl_2$ (150 mL). The organic extract was washed with water (25 mL) and brine (25 mL), dried over $MgSO_4$, and evaporated to dryness. The residue was purified by flash chromatography over silica gel using $CH_2Cl_2$/acetone (7:3) as eluent. The pure fractions were pooled together and evaporated to give 2 g (60%) of 29 as foam: $^1H$ NMR ($Me_2SO$-$d_6$) δ0.80 (m, 3H, $CH_3$), 0.96 (m, 6H, Isobutyryl $CH_3$), 1.16 (m, 12H, 6 $CH_2$), 1.36 (m, 2H, $CH_2$), 2.32 (m, 1H, $C_2$·H), 2.60 (m, 1H, Isobutyryl CH), 2.72 (m, 1H, $C_2$·H), 3.12 (m, 2H, $CH_2$), 3.52 (m, 2H, $C_5$·$CH_2$), 3.70 (2 d, 6H, 2$OCH_3$), 3.90 (m, 1H, $C_4$·H), 4.34 (m, 1H, $C_3$·H), 5.36 (m, 1H, $C_3$·OH), 6.26 (t, 1H, $J_{1',2'}$=6.20 Hz, $C_1$·H), 6.70–7.36 (m, 13H, ArH), 8.18 (s, 1H, $C_8$H). Anal. Calcd for $C_{44}H_{56}N_5O_7$: C, 68.90; H, 7.36; N, 9.31. Found: C, 68.76; H, 7.47; N, 9.09.

EXAMPLE 29

3'-O-[(N,N-Diisopropylamino)(β-cyanoethoxy)phosphanyl]-5'-O-(4,4'-dimethoxytrityl)-$N_2$-isobutyryl-$N_2$-nonyl-9-(2'-deoxy-β-D-erythro-pentofuranosyl)guanosine. (30)

A well dried solution of 29 (1.7 g, 2.22 mmol) in dry dichloromethane (30 mL) was cooled to 0° C. To this cold solution was added N,N-diisopropyethylamine (0.57 g, 4.4 mmol) and (β-cyanoethoxy)chloro(N,N-diisopropylamino)phosphane (0.94 g, 4.0 mmol) under argon atmosphere. The reaction mixture was stirred at room temperature for 2 hours and diluted with $CH_2Cl_2$ (170 mL). The organic extract was washed with 5% $NaHCO_3$ (25 mL), water (25 mL) and brine (25 mL), dried over $Na_2SO_4$, and evaporated to dryness. The residue was purified on a silica column using $CH_2Cl_2$/acetone (9:1) containing 1% triethylamine as eluent. The pure fractions were pooled together and evaporated to dryness to give 1.5 g (53%) of 30.

EXAMPLE 30

3',5'-O-(Tetraisopropyldisiloxane-1,3-diyl)-2-chloro-9-(2'-deoxy-β-D-erythro-pentofuranosyl)adenosine. (31)

Compound 31 was prepared from compound 10 by following the procedure used for the preparation of 12. Starting materials used: 10 (4.30 g, 15.09 mmol), 1,3-dichloro-1,1,3,3-tetraisopropyldisiloxane (4.74 g, 15.1 mmol), dry TEA (3.05 g, 30.2 mmol), and dry pyridine (100 mL). The crude product was purified by flash chromatography using $CH_2Cl_2$/acetone (7:3) as eluent to give 7.3 g (92%) of 31. The pure product was crystallized from ethylacetate/hexane as a colorless solid. mp 183°–185° C.: $^1H$ NMR ($Me_2SO-d_6$) δ1.00 (m, 28H), 2.54 (m, 1H, $C_2H$), 2.82 (m, 1H, $C_2H$), 3.76 (m, 1H, $C_4H$), 3.86 (m, 2H, $C_5CH_2$), 5.08 (m, 1H, $C_3H$), 6.22 (t, 1H, $J_{1',2'}$=6.20 Hz, $C_1H$), 7.82 (b s, 2H, $NH_2$), 8.22 (s, 1H, $C_8H$). Anal. Calcd for $C_{22}H_{38}ClN_5O_4Si_2$: C, 50.02; H, 7.25; N, 13.26, Cl, 6.72. Found: C, 50.24; H, 7.28; N, 13.07, Cl, 6.63.

EXAMPLE 31

3',5'-O-(Tetraisopropyldisiloxane-1,3-diyl)-2-chloro-$N_6$-benzoyl-9-(2'-deoxy-β-D-erythro-pentofuranosyl)adenosine. (32)

A well dried solution of 31 (8 g, 15.00 mmol) in dry pyridine (150 mL) was allowed to react with triethylamine (4.55 g, 45.00 mmol) and benzoyl chloride (6.3 g, 45.00 mmol) at room temperature for 12 hours under argon atmosphere. The reaction mixture was evaporated to dryness. The residue was partitioned between $CH_2Cl_2$/water and extracted in $CH_2Cl_2$ (2×150 mL). The organic extract was washed with brine (60 mL), dried over $MgSO_4$ and evaporated to dryness. The residue was purified by silica column using $CH_2Cl_2$/acetone as eluent and crystallization from the same solvent gave 8.2 g (86%) of 32. mp 167°–170° C.: $^1H$ NMR ($Me_2SO-d_6$) δ1.00 (m, 28H), 2.60 (m, 1H, $C_2H$), 3.02 (m, 1H, $C_2H$), 3.84 (m, 3H, $C_5CH_2$ and $C_4H$), 5.04 (m, 1H, $C_3H$), 6.34 (d, 1H, $C_1H$), 7.42–7.84 (m, 5H, ArH), 8.70 (s, 1H, $C_8H$). Anal. Calcd for $C_{29}H_{42}ClN_5O_5Si_2$: C, 55.08; H, 6.69; N, 11.08, $Cl_{5.61}$. Found: C, 55.21; H, 6.79; N, 11.19, Cl, 5.70.

EXAMPLE 32

$N_6$-Benzoyl-2-chloro-9-(2'-deoxy-β-D-erythro-pentofuranosyl)adenosine. (33)

To a stirred solution of 32 (7.9 g, 12.5 mmol) in dry THF (100 mL) was added 1M solution of tetrabutylammonium fluoride (50 mL, 50.00 mmol) slowly over a 15 minute period at room temperature. The reaction mixture was stirred for 6 hours and evaporated to dryness. The residue was purified by flash chromatography using $CH_2Cl_2$/acetone (7:3) as eluent to give 3.88 g (80%) of 33. mp >275° C. dec: $^1H$ NMR ($Me_2SO-d_6$) δ 2.34 (m, 1H, $C_2H$), 2.72 (m, 1H, $C_2H$), 3.58 (m, 2H, $C_5CH_2$), 3.88 (m, 1H, $C_4H$), 4.42 (m, 1H, $C_3H$), 4.96 (t, 1H, $C_5OH$), 5.38 (d, 1H, $C_3OH$), 6.40 (t, 1H, $J_{1',2'}$=6.20 Hz, $C_1H$), 7.52 (m, 2H, ArH), 7.64 (m, 1H, ArH), 8.04 (d, 2H, ArH), 8.70 (s, 1H, $C_8H$), 11.52 (b s, 1H, NH). Anal. Calcd for $C_{17}H_{16}ClN_5O_4$: C, 52.37; H, 4.14; N, 17.97; Cl, 9.11. Found: C, 52.31; H, 4.07; N, 17.94; Cl, 9.03.

EXAMPLE 33

5'-O-(4,4'-Dimethoxytrityl)-$N_6$-benzoyl-2-chloro-9-(2'-deoxy-β-D-erythro-pentofuranosyl)adenosine. (34)

The compound was prepared from 33 by following the procedure used for the preparation of 8. Starting materials used: 33 (2.5 g. 6.43 mmol), 4,4'-dimethoxytrityl chloride (2.37 g, 7.0 mmol), dry TEA (0.71 g, 7.0 mmol) and dry pyridine (100 mL). The crude product was purified by flash chromatography using $CH_2Cl_2$/EtOAc (7:3) containing 1% triethylamine as the eluent to give 3 g (68%) of 34 as foam: $^1H$ NMR ($Me_2SO-d_6$) δ2.34 (m, 1H, $C_2H$), 2.82 (m, 1H, $C_2H$) 3.18 (m, 2H, $C_5CH_2$), 3.64 (2 d, 6H, $OCH_3$), 3.98 (m, 1H, $C_4H$), 4.44 (m, 1H, $C_3H$), 5.40 (d, 1H, OH), 6.42 (t, 1H, $J_{1',2'}$=6.20 Hz, $C_1H$), 6.74 (m, 4H, ArH), 7.16 (m, 7H, ArH), 7.32 (m, 2H, ArH), 7.52 (m, 7H, ArH), 7.64 (m, 1H, ArH), 8.04 (m, 2H, ArH), 8.58 (s, 1H, $C_8H$), 11.50 (b s, 1H, NH). Anal. Calcd for $CH_{38}H_{34}ClN_5O_6$: C, 65.93; H, 4.95; N, 10.12; Cl, 5.13. Found: C, 65.55; H, 5.16; N, 9.73; Cl, 5.10.

EXAMPLE 34

3'-O-[(N,N-DiisoPropylamino)(β-cyanoethoxy)phosphanyl]-5'-O-(4,4'-dimethoxytrityl)-$N_6$-benzoyl-2-chloro-9-(2'-deoxy-β-D-erythro-pentofuranosyl)adenosine. (35)

The title compound was prepared from 34 by following the procedure used for the preparation of 9. Starting materials used: Compound 34 (2.4 g, 3.47 mmol), N,N-diisopropylethylamine (1.22 mL, 7.00 mmol), (β-cyanoethoxy) chloro(N,N-diisopropylamino)phosphene (1.65 g, 7.00 mmol) and dry $CH_2Cl_2$ (30 mL). The crude product was purified by flash chromatography using hexane-ethyl acetate (1:1) containing 1% triethylamine as eluent. The pure fractions were pooled together and evaporated to dryness to give 1.8 g (58%) of 35. The foam was dissolved in dry dichloromethane (10 mL) and added dropwise into a well stirred hexane (1500 mL) under argon atmosphere. After the addition, stirring was continued for an additional 1 hour and the precipitated solid was filtered, washed with hexane and dried over solid NaOH for 3 hours. The dried powder showed no traces of impurity in $^{31}P$ spectrum: $^1H$ NMR ($Me_2SO-d_6$) δ1.18 (m, 12H, Isobutyryl $CH_3$), 2.58 (m, 3H, $C_2H$ and Isobutyryl CH), 2.98 (m, 1H, $C_2H$), 3.34 (d, 2H, $CH_2$), 3.64 (m, 2H, $C_5CH_2$), 3.72 (m, 8H, $OCH_3$ and $CH_2$), 4.24 (m, 1H, $C_4H$), 4.82 (m, 1H, $C_3H$), 6.36 (t, 1H, $J_{1',2'}$=6.20 Hz, $C_1H$), 6.76 (m, 4H, ArH), 7.22 (m, 7H, ArH), 7.38 (m, 2H, ArH), 7.52 (m, 2H, ArH), 7.64 (m, 1H, ArH), 7.98 (m, 2H, ArH), 8.24 (s, 1H, $C_8H$), 9.34 (b s, 1H, NH).

EXAMPLE 35

3',5'-O-(Tetraisopropyldisiloxane-1,3-diyl)-$N_2$-ethyl-9-(2'-deoxy-β-D-erythro-pentofuranosyl)guanosine. (36)

A solution of 3',5'-O-(tetraisopropyldisiloxane-1, 3-diyl)-2-chloro-9-(2'-deoxy-β-D-erythro-pentofuranosyl)inosine (5.0 g, 9.45 mmol) in 2-methoxyethanol (30 mL) was placed in a steel bomb and cooled to 0° C. Freshly condensed ethylamine (7.0 mL) was quickly added. The steel bomb was sealed and the reaction mixture was stirred at 90° C. for 16 hours. The vessel was cooled and opened carefully. The precipitated white solid was filtered and crystallized from methanol. The filtrate on evaporation gave solid which was also crystallized from methanol. Total yield 3. g (65%). mp >250° C. dec: $^1H$ NMR ($Me_2SO-d_6$) δ1.06 (m, 31H), 2.32 (m, 1H, $C_2H$), 2.84 (m, 1H, $C_2H$), 3.26 (m, 2H, $CH_2$), 4.12 (m, 2H, $C_5CH_2$), 4.22 (m, 1H, $C_4H$), 4.70 (m, 1H, $C_3H$), 6.23 (t, 1H, $J_{1',2'}$=6.20 Hz, $C_1H$), 6.42 (m, 1H, NH), 7.87 (s, 1H, $C_8H$), 10.58 (b s, 1H, NH). Anal. Calcd for $C_{24}H_{43}N_5O_5Si_2$. C, 53.59; H, 8.06; N, 13.02. Found: C, 53.44; H, 8.24; N, 12.91.

EXAMPLE 36

3',5'-O-(Tetraisopropyldisiloxane-1,3-diyl)-6-O-diphenylcarbamoyl-$N_2$-ethyl-9-( 2'-deoxy-β-D-erythro-pentofuranosyl)guanosine. (37)

Compound 36 (2.40 g, 4.46 mmol) was dissolved in anhydrous pyridine (30 mL) at room temperature. To this solution was added N,N-diisoproylethylamine (1.60 mL, 8.93 mmol) followed by diphenylcarbamoyl chloride (2.07 g, 8.93 mmol). The mixture was stirred at room temperature under argon atmosphere for 10 hours. A dark red solution was obtained, which was evaporated to dryness. The residue was purified by flash chromatography on a silica column using $CH_2Cl_2$/EtoAc as eluent. The pure fractions were collected together and evaporated to give a brownish foam (3.25 g, 99%). $^1$H NMR ($Me_2SO-d_6$) δ1.14 (t, 31H), 2.52 (m, 1H, $C_2$.H), 3.04 (m, 1H, $C_2$.H), 3.34 (m, 2H, $CH_2$), 3.87 (m, 3H, $C_5$.$CH_2$ & $C_4$.H), 4.83 (m, 1H, $C_3$.H), 6.23 (m, 1H, $C_1$.H), 7.36 (m, 11H, ArH & NH), 8.17 (s, 1H, $C_8$H). Anal. Calcd for $C_{37}H_{52}N_6O_6Si_2$. C, 60.71; H, 7.16; N, 11.48. Found: C, 60.33; H, 7.18; N, 11.21.

EXAMPLE 37

6-O-Diphenylcarbamoyl-$N_2$-ethyl-9-(2'-deoxy-β-D-erythro-pentofuranosyl)guanosine. (38)

To a stirred solution of 37 (3.25 g, 4.47 mmol) in pyridine (25 mL) was added 0.5M solution of tetrabutylammonium fluoride (prepared in pyridine/THF/water, 4/1/1,36 mL, 17.88 mmol) at once. The reaction was allowed to stir for 10 minutes and quenched with $H^+$ resin (amberlite IRC 50) to pH 7. The resin was filtered and washed with pyridine (20 mL) and MeOH (20 mL). The filtrate was evaporated to dryness. The residue was purified using flash chromatography over a silica column using methylene chloride-acetone as eluent to give 1.84 g (84%) of the pure product as foam. $^1$H NMR ($Me_2SO-d_6$) δ1.14 (t, 3H, $CH_2CH_3$), 2.22 (m, 1H, $C_2$.H), 2.76 (m, 1H, $C_2$.H), 3.34 (m, 2H, $CH_2$), 3.57 (m, 2H, $C_5$.$CH_2$), 3.84 (m, 1H, $C_4$.H), 4.42 (m, 1H, $C_3$.H), 4.91 (t, 1H, $C_5$.OH), 5.32 (d, 1H, $C_3$.H), 6.27 (t, 1H, $J_{1',2'}$=6.20 Hz $C_1$.H), 7.29 (m, 1H, NH), 7.46 (m, 10H, ArH), 8.27 (s, 1H, $C_8$H). Anal. Calcd for $C_{25}H_{26}N_6O_5$.3/4$H_2O$. C, 59.61; H, 5.35; N, 16.68. Found: C, 59.83; H, 5.48; N, 16.21.

EXAMPLE 38

$N_2$-Ethyl-9-(2'-deoxy-β-D-erythro-pentofuranosyl)guanosine. (39)

The intermediate of 38 (0.25 g, 0.51 mmol) was stirred in methanolic/ammonia (saturated at 0° C.) in a steel bomb at room temperature for 40 hours. The vessel was cooled to 0° C., opened carefully, and the solvent evaporated to dryness. The solid obtained was crystallized from methanol to give a white powder (0.95 g, 63%): mp 234°–238° C. $^1$H NMR ($Me_2SO-d_6$) δ1.14 (t, 3H, $CH_2CH_3$), 2.18 (m, 1H, $C_2$.H), 2.67 (m, 1H, $C_2$.H), 3.34 (m, 2H, $CH_2$), 3.52 (m, 2H, $C_5$.$CH_2$), 3.82 (m, 1H, $C_4$.H), 4.36 (m, 1H, $C_3$.H), 4.89 (t, 1H, $C_5$.OH), 5.30 (d, 1H, $C_3$.H), 6.16 (t, 1H, $J_{1',2'}$=6.20 Hz $C_1$.H), 6.44 (m, 1H, NH), 7.91 (s, 1H, $C_8$H), 10.58 (b s, 1H, NH).

EXAMPLE 39

5'-O-(4,4'-Dimethoxytrityl)-6-O-diphenylcarbamoyl-$N_2$-ethyl-9-(2'-deoxy-β-D-erythro-pentofuranosyl)guanosine. (40)

Compound 38 (1.6 g, 3.26 mmol) was dried well by coevaporation with dry pyridine (3×50 mL). The dried material was dissolved in anhydrous pyridine (25 mL) and allowed to stir under argon atmosphere. To this stirred solution was added triethylamine (0.59 mL, 4.24 mmol) followed by DMTCl (1.44 g, 4.24 mmol). The reaction mixture was stirred at room temperature for 14 hours and quenched with methanol (10 mL). After stirring for 15 minutes, the solvent was removed and the residue was dissolved in methylene chloride (150 mL). The organic extract was washed with saturated $NaHCO_3$ solution (30 mL), water (30 mL), and brine (30 mL). The methylene chloride extract was dried and evaporated to dryness. The residue was purified by flash chromatography over silica gel using methylene chloride/acetone as eluent. The pure fractions were collected together and evaporated to give a foam (2.24 g, 87%). $^1$H NMR ($Me_2SO-d_6$) δ1.10 (t, 3H, $CH_2CH_3$), 2.32 (m, 1H, $C_2$.H), 2.82 (m, 1H, $C_2$.H), 3.15 (m, 2H, $CH_2$), 3.34 (s, 6H, 2$OCH_3$), 3.67 (m, 2H, $C_5$.$CH_2$), 3.96 (m, 1H, $C_4$.H), 4.42 (m, 1H, $C_3$.H), 5.36 (d, 1H, $C_3$.OH), 6.30 (t, 1H, $J_{1',2}$=6.20 Hz, $C_1$.H), 6.83 (m, 4H, ArH), 7.23 (m, 10H, ArH & NH), 8.17 (s, 1H, $C_8$H). Anal Calcd for $C_{45}H_{44}N_6O_7$. 1/4 $CH_3OH$. 1/4 $H_2O$. C, 68.50; H, 5.78; N, 10.60. Found: C, 68.72; H, 5.42; N, 10.40.

EXAMPLE 40

3'-O-[(N,N-Diisopropylamino)(β-cyanoethoxy)phosphanyl]-5'-O-(4,4'-dimethoxytrityl)-6-O-diphenylcarbamoyl-$N_2$-ethyl-9-(2'-deoxy-β-D-erythro-pentofuranosyl)guanosine. (41)

The DMT derivative of 40 was dried well overnight at vacuum and dissolved in dry methylene chloride (25 mL). The solution was cooled to 0° C. under argon atmosphere. To this cold stirring solution N,N-diisopropylamine tetrazolide salt (0.24 g, 1.41 mmol) followed by phosphorylating reagent (1.71 mL, 5.66 mmol) were added. The mixture was stirred at room temperature for 12 hours under argon. The solution was diluted with additional methylene chloride (100 mL) and washed with saturated $NaHCO_3$ solution (50 mL), water (50 mL), and brine (50 mL). The organic extract was dried and evaporated to dryness. The crude product was purified by flash column over silica gel using methylene chloride/ethyl acetate containing 1% triethylamine as eluent. The pure fractions were pooled and evaporated to give 2.5 g (91%) of 41.

EXAMPLE 41

3',5'-Di-O-acetyl-$N_2$-acetyl-9-(2'-deoxy-β-D-erythro-pentofuranosyl)guanosine. (42)

Deoxyguanosine (26.10 g, 96.77 mmol) was coevaporated with dry pyridine/DMF (50 mL each) three times. The residue was suspended in dry DMF (50 mL) and dry pyridine (50 mL) at room temperature. To this stirring mixture was added N,N-dimethylaminopyridine (1.18 g, 9.67 mmol) followed by acetic anhydride (109.6 mL, 116 mmol) slowly keeping the temperature below 35° C. After the addition of $Ac_2O$, the reaction was placed at 80° C. for 4 hours under argon. It was cooled to room temperature and neutralized with 1N $NaCO_3$ solution. The mixture was extracted in $CH_2Cl_2$ (2×250 mL). The organic extract was washed with water (50 mL) and brine (50 mL), dried, and evaporated to dryness. The residue was crystallized from MeOH to give 29.1 g (76%): mp 217°–219° C. $^1$H NMR ($Me_2SO-d_6$) δ 2.04 (s, 3H, $COCH_3$), 2.09 (s, 3H, $COCH_3$), 2.19 (s, 3H, $COCH_3$), 2.60 (m, 1H, $C_2$.H), 3.02 (m, 1H, $C_2$.H), 4.19 (m, 3H, $C_4$.H & $C_5$.$CH_2$), 5.31 (m, 1H, $C_3$.H), 6.21 (t, 1H, $J_{1',2'}$ =6.00 Hz, $C_1$.H), 8.27 (s, 1H, $C_8$H), 11.72 (b s, 1H, NH), 12.02 (b s, 1H, NH).

EXAMPLE 42

6-O-Benzyl-9-(2'-deoxy-β-D-erythro-pentofuranosyl)guanosine. (43)

$N_2$,3',5'-Tri-O-acetyldeoxyguanosine 42 (1.18 g, 3 mmol) was suspended in dry dioxane (50 mL) under argon atmosphere. To this stirred suspension was added dry benzyl alcohol (0.81 g, 7.5 mmol) followed by triphenyl phosphine (1.96 g, 7.5 mmol). After stirring for 15 minutes, diethylazodicarboxylate (1.30 g, 7.5 mmol) was added dropwise over a 15 minute period at room temperature. The reaction mixture was stirred under argon overnight at room temperature. The solvent was removed and the residue treated with 0.1M sodium methoxide (75 mL) and stirred at room temperature overnight. Glacial acetic acid (0.45 mL) was added, the solvents were evaporated and the residue was partitioned between water and ethyl acetate. The ethyl acetate extracts were dried, evaporated and the residue was chromatographed over silica gel using $CH_2Cl_2$—MeOH mixture. The product (0.5 g, 75%) was obtained as an amorphous white solid after trituration with ether. $^1H$ NMR ($Me_2SO-d_6$) $\delta 2.22$ (m, 1H, $C_2 H$), 2.60 (m, 1H, $C_2 H$), 3.56 (m, 2H, $C_5 CH_2$), 3.80 (m, 1H, $C_4 H$), 4.37 (m, 1H, $C_3 H$), 5.01 (t, 1H, $C_5 OH$), 5.29 (b s, 1H, $C_3 H$), 5.52 (s, 2H, $ArCH_2$), 6.23 (t, 1H, $J_{1',2'}=6.66$ Hz, $C_1 H$), 6.52 (b s, 2H, $NH_2$), 7.40 (m, 2H, ArH), 7.50 (m, 2H, ArH), 8.11 (s, 1H, $C_8 H$). Anal. Calcd for $C_{17}H_{19}N_5O_4$. C, 57.13; H, 5.36; N, 19.59. Found: C, 57.09; H, 5.42; N, 19.61.

EXAMPLE 43

6-O-Benzyl-2-fluoro-9-(2'-deozy-β-D-erythro-pentofuransoyl)purine. (44)

To a stirred suspension of the substrate 43 (5.0 g, 14 mmol) in dry pyridine (20 ml) at −40° C. was added HF/pyridine (Aldrich 18,422-5 70%) in two portions (2×10 mL) under argon atmosphere. After the addition of HF/pyridine, the mixture was warmed up to −10° C., during that time all the solid had gone into solution. Tert-butyl nitrite (4.0 mL) was added slowly during the course of 10 minutes maintaining the temperature between −20° C. and −10° C. At intervals the reaction mixture was removed from the cooling bath and swirled vigorously to ensure thorough mixing. After complete conversion of the starting material (checked by TLC at 15 minute intervals), the reaction mixture was poured onto a vigorously stirred ice cold alkaline solution (70 g of $K_2CO_3$ in 150 mL of water). The gummy suspension was extracted with methylene chloride (2×200 mL). The organic extract was washed with brine (100 mL), dried and evaporated to dryness. The residue was purified by flash chromatography over silica gel using $CH_2Cl_2$ MeOH as eluent. The pure fractions were combined and evaporated to give 4.0 g (79%) of 44 as foam. A small quantity was crystallized from methanol as orange crystals. mp: 165°–167° C. $^1H$ NMR ($Me_2SO-d_6$) $\delta 2.36$ (m, 1H, $C_2 H$), 2.66 (m, 1H, $C_2 H$), 3.60 (m, 2H, $C_5 CH_2$), 3.87 (m, 1H, $C_4 H$), 4.42 (m, 1H, $C_3 H$), 4.95 (t, 1H, $C_5 OH$), 5.36 (d, 1H, $C_3 OH$), 5.62 (s, 2H, $ArCH_2$), 6.34 (t, 1H, $J_{1',2'}=6.67$ Hz, $C_1 H$), 6.46 (m, 4H, ArH), 8.61 (s, 1H, $C_8 H$). Anal. Calcd for $C_{17}H_{17}FN_4O_4$. C, 56.66; H, 4.76; N, 15.55. Found: C, 56.62; H, 4.69; N, 15.50.

EXAMPLE 44

5'-O-(4,4'-Dimethoxytrityl)-2-fluoro-9-(2'-deoxy-β-D-erythro-pentofuranosyl)inosine. (45)

Compound 44 (5.00 g, 13.89 mmol) was dissolved in methanol (100 mL) and placed in a parr bottle. To this solution Pd/C (5%, 1.00 g) was added and hydrogenated at 45 psi for 2 hours. The suspension was filtered, washed with methanol (50 mL) and the combined filtrate evaporated to dryness. The residue was dissolved in dry pyridine (50 mL) and evaporated to dryness. This was repeated three times and the resulting residue (weighed 4.00 g) was dissolved in dry pyridine (100 mL) under argon atmosphere. To this stirred solution was added triethylamine (1.52 g, 15.0 mmol) and 4,4'-dimethoxytrityl chloride (5.07 g, 15.0 mmol) at room temperature. The reaction mixture was allowed to stir at room temperature under argon atmosphere overnight. It was quenched with methanol (20 mL) and evaporated to dryness. The residue was dissolved in methylene chloride (200 ml) and washed with 5% $NaHCO_3$ solution (50 mL), water (50 mL), and brine (50 mL). The organic extract was dried, and evaporated to dryness. The residue was suspended in dichlormethane and the insoluble solid filtered. The filtrate was purified by flash chromatography over silica gel using $CH_2Cl_2$ MeOH as the eluent. The pure fractions were collected and evaporated to give 7.0 g (88%) of the title compound. The insoluble solid was found to be the DMT derivative. mp>220° C. dec: $^1H$ NMR ($Me_2SO-d_6$) $\delta 2.22$ (m, 1H, $C_2 H$), 2.70 (m, 1H, $C_2 H$), 3.16 (m, 2H, $C_5 CH_2$), 3.90 (m, 1H, $C_4 H$), 4.38 (m, 1H, $C_3 H$), 5.32 (d, 1H, $C_3 OH$), 6.16 (t, 1H, $J_{1',2'}=6.20$ Hz, $C_1 H$), 6.82 (m, 4H, ArH), 7.25 (m, 9H, ArH), 7.79 (s, 1H, $C_8 H$).

EXAMPLE 45

3'-O-[(N,N-Diisopropylamino)(β-cyanoethoxy)phosphanyl]-5'-O-(4,4'-dimethoxytrityl)-2-flouro-9-(2'-deoxy-β-D-erythro-pentofuranosyl)inosine. (46)

The title compound was prepared from 45 by following the procedure used for the preparation of 9. Starting materials used: 45 (7.0 g, 12.24 mmol), N,N-diisopropylethylamine (5.2 mL, 30.00 mmol), (β-cyanoethoxy) chloro (N,N-diisopropylamino)phosphane (5.9 g, 25.00 mmol) and dry $CH_2Cl_2$ (100 mL). The crude product was purified by flash chromatography using dichloromethane/methanol (95:5) containing 1% triethylamine as eluent. The pure fractions were pooled together and evaporated to dryness to give 7.00 g (75.5%) of 46. The foam was dissolved in dry dichloromethane (30 mL) and added dropwise into a well stirred hexane (2500 ml) under argon atmosphere. After the addition, stirring was continued for additional 1 hour and the precipitated solid was filtered, washed with hexane and dried over solid NaOH for 3 hours. The dried powder showed no traces of impurity in $^3P$ spectrum.

SCHEME 1

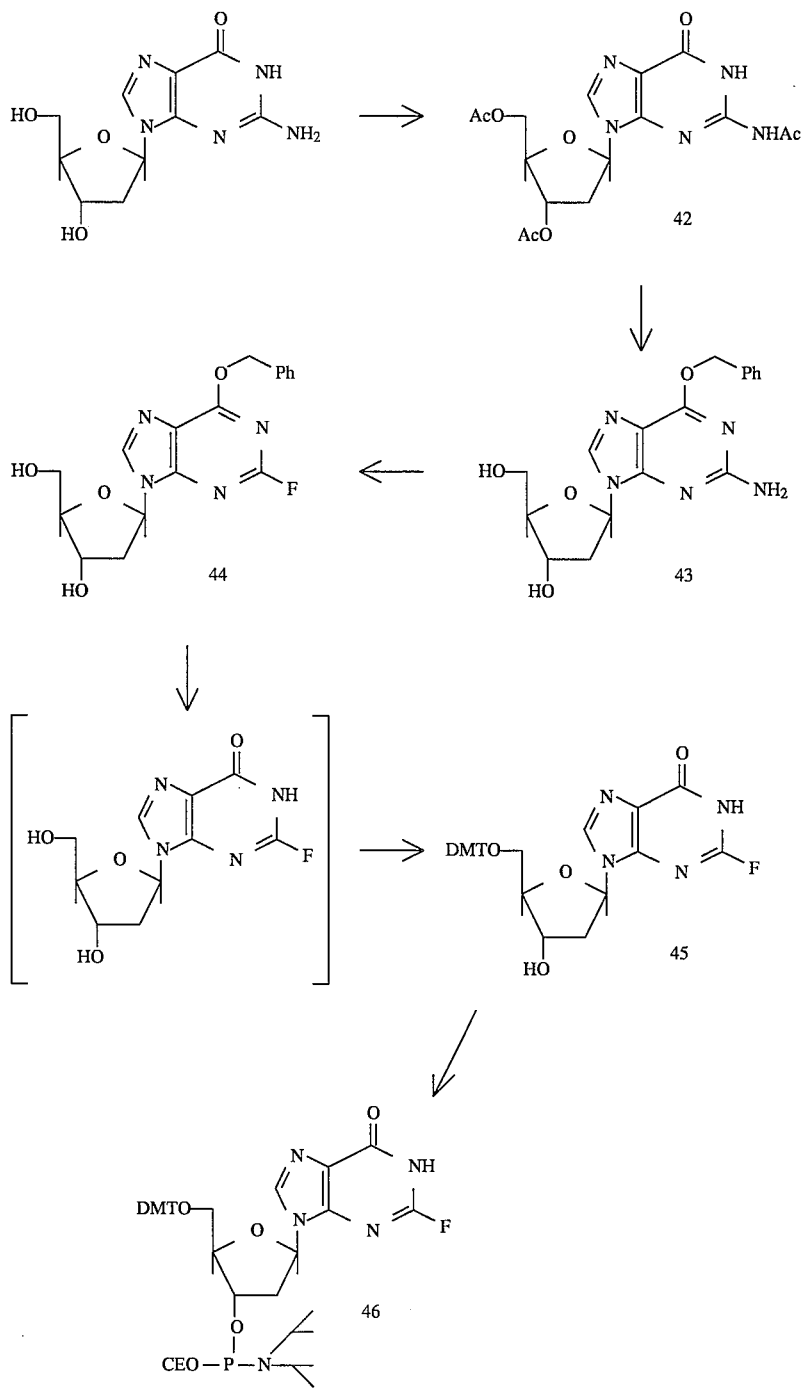

EXAMPLE 46

N-[N-(tert-Butyloxycarbonyl)-3-aminopropyl]benzylamine (47).

A solution of N-(3-aminopropyl)benzylamine (38 g, 231.71 mmoles) in dry tetrahydrofuran (300 mL) was cooled to 5° C. in an ice-alcohol bath. To this cold stirred solution 2-[[(tert-butyoxycarbonyl)oxy]imino]-2-phenylacetonitrile (BOC-ON) (56.58 g, 230 mmoles) in dry tetrahydrofuran (300 mL) was added slowly during a 6 hour period. After the addition of BOC-ON, the reaction mixture was stirred at room temperature under argon for an additional 6 hours. The reaction mixture was evaporated to dryness and the residue was dissolved in ether (750 mL). The ether extract was washed with 5% sodium hydroxide solution (4×100 mL), dried over anhydrous sodium sulfate, and concentrated to dryness. The residue was purified by flash column using a chromatography over a silica dichloromethane→methanol gradient. The pure fractions were pooled together and evaporated to give 49.5 g (81%) of product as oil: $^1$H nmr (deuteriochloroform): δ1.42 (s, 9H, t-Boc), 1.65 (m, 2H, $CH_2CH_2CH_2$), 2.70 (t, 2H, $CH_2NHCH_2$), 3.20 (m, 2H, $BocNHCH_2$), 3.78 (s, 2H, $ArCH_2$), 5.32 (br s, 1H, BocNH), 7.30 (m, 5H, ArH).

EXAMPLE 47

10-Cyano-9-(phenylmethyl)-2,2-dimethyl-3-oxa-4-oxo-5,9-diazadecane (48).

To a stirred solution of the compound 47 (24 g, 91 mmoles) in dry acetonitrile (500 ml) was added potassium/celite (50 g) and chloroacetonitrile (27.3 g, 364 mmoles) at room temperature. The reaction mixture was placed in a preheated oil bath at 85° C. and allowed to stir at that temperature under argon for 12 hours. The reaction mixture was cooled, filtered and washed with dichloromethane (100 mL). The combined filtrate was evaporated to dryness. The residue was dissolved in dichloromethane (100 mL) and washed with 5% sodium bicarbonate solution (100 mL), water (100 mL) and brine (100 mL). The organic extract was dried over anhydrous sodium sulfate and concentrated to give a solid. The solid was crystallized from dichloromethane/hexane to give 24 g ((87%) as colorless needles, mp 70°–73° C.; $^1$H nmr (deuteriochloroform): δ1.44 (s, 9H, t-Boc), 1.71 (m, 2H, $CH_2CH_2CH_2$), 2.67 (t, 2H, J=6.4 Hz, $CH_2NHCH_2$), 3.23 (m, 2H,$BocNHCH_2$), 3.46 (s, 2H, $CH_2CN$), 3.65 (s, 2H, $ArCH_2$), 4.85 (br s, 1H, BocNH), 7.33 (s, 5H, ArH).

Anal. Calcd. for $C_{17}H_{25}N_3O_2$: C, 67.29; H, 8.31; N, 13.85, Found: C, 67.34; H, 8.45; N, 13.85.

EXAMPLE 48

9,12-Di(phenylmethyl)-2,2-dimethyl-3-oxa-4-oxo-5,9,12-triazadodecane (49).

The nitrile compound of Example 47 (34 g, 112.21 mmoles) was dissolved in ethanol (100 mL) and placed in a parr hydrogenation bottle. Sodium hydroxide (7 g) was dissolved in water (20 mL), mixed with ethanol (180 mL) and added into the parr bottle. Ra/Ni (5 g, wet) was added and shaked in a parr apparatus over hydrogen (45 psi) for 12 hours. The catalyst was filtered, washed with 95% ethanol (100 mL). The combined filtrate was concentrated to 100 mL and cooled to 5° C. in an ice bath mixture. The cold solution was extracted with dichloromethane (3×200 mL). The combined extract dried over anhydrous sodium sulfate and evaporated to give 32 g (92%) of an oil product. The product was used as such for the next reaction. $^1$H nmr (deuteriochloroform): δ1.32 (br s, 2H, $NH_2$), 1.42 (s, 9H, t-Boc), 1.67 (m, 2H, $CH_2CH_2CH_2$), 2.48 (m, 4H, $CH_2CH_2NH_2$), 2.75 (t, 2H, J=6.4 Hz, $CH_2NHCH_2$), 3.15 (m, 2H, $BocNHCH_2$), 3.55 (s, 2H, $ArCH_2$), 5.48 (br s, 1H, BocNH), 7.31 (m, 5H, ArH).

The above amine (33 g, 107.5 mmoles) in dry methanol (100 mL) was mixed with anhydrous magnesium sulfate (30 g) and allowed to stir at room temperature under argon atmosphere. To this stirred solution benzaldehyde (13.2 g, 125 mmoles) was added and the stirring was continued for 4 hours under argon. The reaction mixture was diluted with methanol (150 mL) and cooled to −5° C. in an ice salt bath. Solid sodium borohydride (30 g) was added in 1 g lots at a time during 2 hour periods, keeping the reaction temperature below 0° C. After the addition of sodium borohydride, the reaction mixture was allowed to stir at room temperature overnight and filtered over celite. The filtrate was evaporated to dryness. The residue was partitioned between water (350 mL)/ether (500 mL) and extracted in ether. The ether extract was dried over anhydrous sodium sulfate and evaporated to dryness. The residue was purified on a silica gel column using dichloromethane→methanol as eluent. The pure fractions were pooled together and evaporated to give 35 g (82%) as oil; $^1$H nmr (deuteriochloroform): δ1.42 (s, 9H, t-Boc), 1.65 (m, 2H, $CH_2CH_2CH_2$), 1.75 (br s, 1H, $ArCH_2NH$), 2.55 (m, 4H,$CH_2CH_2$, 2.70 (t, 2H, J=6.4 Hz, $CH_2NHCH_2$), 3.15 (m, 2H, $BocNHCH_2$), 3.52 (s, 2H, $ArCH_2$), 3.72 (s, 2H, $ArCH_2$), 5.55 (br s, 1H, BocNH), 7.28 (m, 10H, ArH).

Anal. Calcd. for $C_{24}H_{35}N_3O_2$: C, 72.51; H, 8.87; N, 10.57. Found: C, 72.39; H, 8.77; H, 10.72.

EXAMPLE 49

13-cyano-9,12-di(phenylmethyl)-2,2-dimethyl-3-oxa-4-oxo-5,9,12-triazatridecane (50).

The title compound was prepared from compound 49 by following the procedure used for the preparation of the compound of Example 47. Materials used: Substrate 49 (4.55 g, 11.46 mmoles); chloro acetonitrile (2.6 g, 34.38 mmoles); potassium fluoride/celite (9.0 g) and dry acetonitrile (100 mL). The crude product was purified by flash chromatography over silica gel using dichloromethane→acetone as the eluent to give 4.8 g (96%); $^1$H nmr (deuteriochloroform): δ1.42 (s, 9H, t-Boc), 1.68 (m, 2H, $CH_2CH_2CH_2$), 2.52 (m, 4H, $CH_2CH_2$), 2.68 (t, 2H, J=6.2 Hz, $CH_2NHCH_2$), 3.22 (m, 2H, $BocNHCH_2$), 3.36 (s, 2H, $CNCH_2$), 3.50 (s, 2H, $ArCH_2$), 3.62 (s, 2H, $ArCH_2$), 5.72 (br s, 1H, BocNH), 7.32 (m, 10H, ArH).

Anal. Calcd. for $C_{26}H_{36}H_4O_2$: C, 71.52; H, 8.31; H, 12.83. Found: C, 71.17; H, 8.14; N, 12.82.

EXAMPLE 50

9,12,15-Tri(phenylmethyl)2,2-dimethyl-3-oxa-4-oxo-5,9,12,15-tetraazapentadecane (51).

The title compound was prepared from compound 50 by following a two step procedure used in Example 48. Materials used in the first step: The substrate 50 (25 g, 57.34 mmoles); Ra/Ni (5 g); sodium hydroxide in ethanol (200 mL, 7 g of sodium hydroxide was dissolved in 20 mL of water and mixed with ethanol) and ethanol used to dissolve the substrate (100 mL). The crude product was extracted in dichloromethane which on evaporation gave 22 g (87%) of an oily product; $^1$H nmr (deuteriochloroform): δ1.40 (s, 9H, t-Boc), 1.50 (m, 4H, $CH_2CH_2CH_2$ & $NH_2$), 2.48 (m, 8H, 2 $CH_2CH_2$), 2.66 (t, 2H, J=6.2 Hz, $CH_2NHCH_2$), 3.24 (m, 2H, $BocNHCH_2$), 3.50 (s, 2H, $ArCH_2$), 3.56 (s, 2H, $ArCH_2$), 5.48 (br s, 1H, BocNH), 7.28 (m, 10H, ArH).

Materials used in the second step: Above amine (24.4 g, 55.33 mmoles); benzaldehyde (6.36 g, 60.00 mmoles); magnesium sulfate (20.0 g) and dry methanol (200 mL). The crude product was purified by flash chromatography over silica gel using dichloromethane→methanol as the eluent to give 20.0 g (68%) of compound 51 as oil; $^1$H nmr (deuteriochloroform): δ1.40 (s, 9H, t-Boc), 1.52 (m, 2H, $CH_2CH_2CH_2$), 1.84 (br s, 1H, $ArCH_2NH$), 2.38 (t, 2H, J=6.2 Hz, $CH_2NHCH_2$), 2.54 (m, 8H 2 $CH_2CH_2$), 3.08 (m, 2H, $BocNHCH_2$), 3.42 (s, 2H, $ArCH_2$), 3.50 (s, 2H, $ArCH_2$), 3.65 (s, 2H, $ArCH_2$), 3.65 (s, 2H, $ArCH_2$), 5.45 (br s, 1H, BocNH), 7.28 (m, 15H, ArH).

Anal. Calcd. for $C_{33}H_{46}N_4O_2$: C, 74.67; H, 8.74; N, 10.56. Found: C, 74.92; H, 8.39; N, 10.71.

EXAMPLE 51

16-Cyano-9,12,15-tri(phenylmethyl)-2,2-dimethyl-3-oxa-oxo-5,9,12,15-tetraazahexadecane (52).

The title compound was prepared from compound 51 by following the procedure used in Example 47. Materials used: Substrate (Example 50 compound 51, 8.30 g, 15.66 mmoles); chloro acetonitrile (3.52 g, 46.98 mmoles); potassium fluoride/celite (10.0 g and dry acetonitrile (150 mL). The crude product was purified by flash chromatography over silica gel using dichloromethane→ethyl acetate as the eluent to give 7.6 g (85%); $^1$H nmr (deuteriochloroform): δ1.42 (s, 9H, t-Boc), 1.60 (m,2H, $CH_2CH_2CH_2$), 2.42 (t, 2H, J=6.2 Hz, $CH_2NHCH_2$), 2.60 (m, 8H, $2CH_2CH_2$), 3.14 (m, 2H, BocNHCH ), 3.38 (s, 2H, $CNCH_2$), 3.48 (s, 2H, $ArCH_2$), 3.54 (s, 2H, $ArCH_2$), 3.60 (s, 2H, $ArCH_2$), 5.42 (br s, 1H, BocNH), 7.26 (m, 15H, ArH).

Anal. Calcd. for $C_{35}H_{47}N_5O_2$: C, 73,77; H, 8.32; N, 12.29. Found: C, 73.69; H, 8.19; N, 12.31.

EXAMPLE 52

9,12,15,18-Tetra(phenylmethyl)-2,2-dimethyl-3-oxa-4-oxo-5,9,12,15,18-petaazaoctadecane (53).

The title compound was prepared from compound 52 by following a two step procedure used for the preparation of the Example 48 compound 49. Materials used in the first step: The substrate (compound 52, 7 g, 12.30 mmoles); Ra/Ni (2 g); sodium hydroxide in ethanol (160 mL, 3.5 g of sodium hydroxide was dissolved in 10 mL of water and mixed with ethanol) and ethanol used to dissolve the substrate (100 ml). The crude product was extracted in dichloromethane which on evaporation gave 5.6 g (79%) as oil; $^1$H nmr (deuteriochloroform): δ1.40 (s, 9H, t-Boc), 1.50 (m, 4H, $CH_2CH_2CH_2$ & $NH_2$), 2.48 (m, 12H, 3 $CH_2CH_2$), 2.66 (m, 2H, $CH_2NHCH_2$), 3.24 (m, 2H, $BocNHCH_2$), 3.50 (s, 2H, $ArCH_2$), 3.56 (s, 4H, 2 $ArCH_2$), 3.62 (s, 2H, $ArCH_2$), 5.48 (br s, 1H, BocNH), 7.28 (m, 15H, ArH).

Material used in the second step: above amine (21.2 g, 36.74 mmoles); benzaldehyde (4.24 g, 40.00 mmoles); magnesium sulfate (10.0 g), dry methanol (200 mL) and sodium borohydride (4.85 g, 128.45 mmoles). The crude product was purified by flash chromatography over silica gel using dichloromethane→methanol as the eluent to give 18.67 g (77%) of compound 53 as oil; $^1$H nmr (deuteriochloroform): δ1.40 (s, 9H, t-Boc), 1.52 (m, 2H, $CH_2CH_2CH_2$), 2.05 (br s, 1H, $ArCH_2NH$), 2.38 (t, 2H, J=6.0 Hz, $CH_2NHCH_2$), 2.54 (m, 12H, 2 $CH_2CH_2$), 3.08 (m, 2H, $BocNHCH_2$), 3.40 (s, 2H, $ArCH_2$), 3.50 (s, 4H, 2 $ArCH_2$), 3.64 (s, 2H, $ArCH_2$), 5.55 (br s, 1H, BocNH), 7.28 (m, 20H, ArH).

Anal. Calcd. for $C_{42}H_{57}N_5O_2$: C, 75.98; H, 8.65; N, 10.55. Found: C, 75.72; H, 8.67; N, 10.39.

EXAMPLE 53

13-amino-1,4,7,10-tetra(phenylmethyl)-1,4,7,10-tetraazatridecane (54).

To a stirred solution of compound 53 (2.65 g, 4 mmoles) in dichloromethane (10 mL) was added trifluoroacetic acid (10 mL) at room temperature. The reaction mixture was allowed to stir at room temperature for 30 minutes and evaporated to dryness. The residue was dissolved in dichloromethane (100 mL) and washed with 5% sodium bicarbonate solution (150 mL) to pH 8, and brine (50 mL). The organic extract was dried over anhydrous sodium sulfate and concentrated to dryness. The oily residue that obtained was used as such for the next reaction. $^1$H nmr (deuteriochloroform): δ1.50 (m, 5H, $CH_2CH_2CH_2$, $NH_2$, & $ArCH_2NH$), 2.38 (t, 2H, J=6.4 Hz, $CH_2NHCH_2$), 2.54 (m, 14H, 7 $CH_2$), 3.52 (s, 2H, $ArCH_2$), 3.56 (s, 4H, 2 $ArCH_2$). 3.62 (s, 2H, $ArCH_2$), 7.28 (m, 20H, ArH).

SCHEME 2

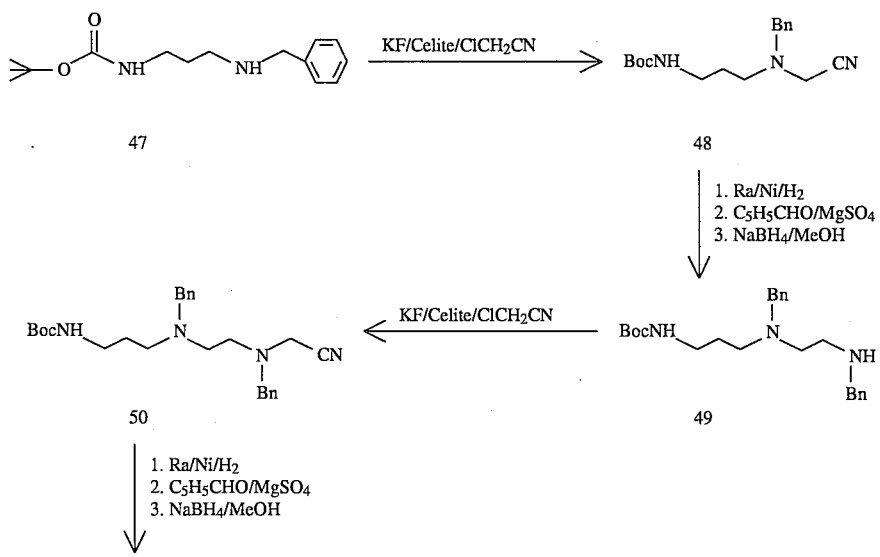

-continued
SCHEME 2

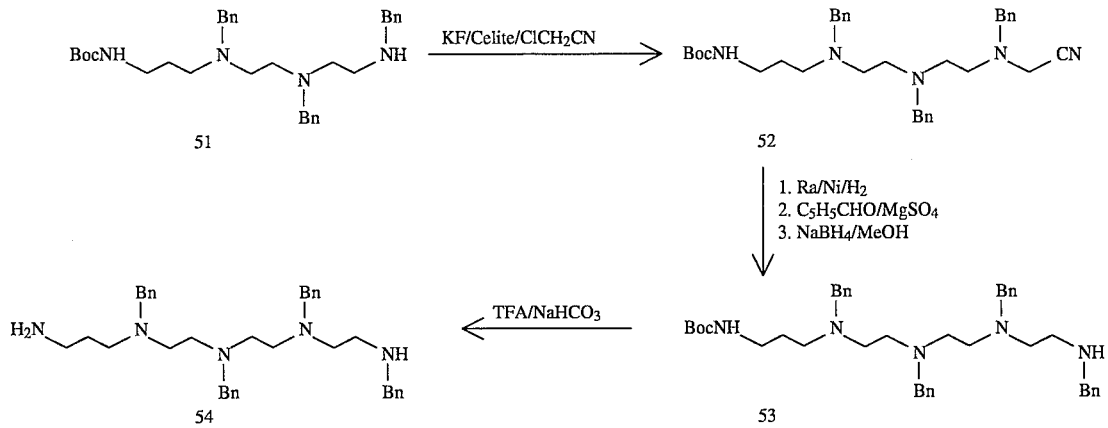

EXAMPLE 54

3',5'-O-(Tetraisopropyldisiloxane-13-diyl)-N-[4,7,10,13-tetrakis-(phenylmethyl)-4,7,10,13-tetraazatridec-1-yl]-2'-deoxyquanosine (56).

A mixture of 2-chloroinosine (55 in reaction scheme 3, 2.12 g, 4 mmoles) and compound 54 (2.5 g, 4.4 mmoles) in 2-methoxyethanol (50 mL) was heated at 80° C. for 12 hours. The reaction mixture was evaporated to dryness and the residue on flash chromatography over silica gel using dichloromethane and methanol (9:1) gave 2.55 g (60%) of the title compound as foam. $^1$H nmr (deuteriochloroform): δ1.00 (m, 24H, 4 Isobutyl-H), 1.62 (m, 1H, $C_2$·H), 1.80 (m, 4H, $CH_2CH_2CH_2$, $C_2$·H, & $ArCH_2NH$), 2.52 (m, 14H, 7 $CH_2$), 3.20 (s, 2H, $ArCH_2$), 3.32 (s, 2H, $ArCH_2$), 3.42 (s, 2H, $ArCH_2$), 3.48 (s, 4H, $ArCH_2$ & $CH_2$), 3.78 (m, 1H, $C_4$·H), 4.05 (m, 2H, $C_5$·$CH_2$), 4.72 (m, 1H, $C_3$·H), 6.22 (m, 1H, $C_1$·H), 6.94 (m. 1H, $N_2$H), 7.26 (m, 20H, ArH), 7.72 (s, 1H, $C_8$H), 10.52 (br s, 1H, NH).

Anal. Calcd. for $C_{59}H_{85}N_9O_5Si_2$: C, 67.07; H, 8.11; N, 11.93. Found: C, 67.22; H, 8.24; N, 11.81.

EXAMPLE 55

3',5'-O-(Tetraisopropyldisiloxane-1,3-diyl)-6-O-(phenylmethyl)-N-[15-methyl-14-oxo-4,7,10,13-tetrakis(phenylmethyl)-4,7,10,13-tetraazahexadec-1-yl] -2'-deoxyguanosine (57).

The compound of Example 54 (2.00 g, 1.89 mmoles) was coevaporated with dry pyridine (30 mL) two times. The resulting residue was dissolved in dry pyridine (50 mL) and cooled to 0° C. in an ice bath mixture. To this cold stirred solution was added triethylamine (0.61 g, 6 mmoles) followed by isobutyryl chloride (0.64 g, 6 mmoles) slowly under argon atmosphere. After the addition of isobutyryl chloride, the reaction mixture was stirred at room temperature for 12 hours and evaporated to dryness. The residue was dissolved in dichloromethane (150 mL), washed with 5% sodium bicarbonate (50 mL), water (50 mL) and brine (50 mL). The organic extract was dried over anhydrous sodium sulfate and evaporated to dryness. The residue on purification over silica gel using dichloromethane/methanol (95:5) gave 1.88 g (88%) of the title compound as a foam.

The above foam (1.8 g, 1.61 mmoles) was dried over phosphorous pentaoxide under vacuum for 12 hours. The dried residue was dissolved in dry dioxane (50 mL) and treated with triphenyl phosphine (0.83 g, 3.2 mmoles), benzyl alcohol (0.35 g, 3.2 mmoles), and diethylazodicarboxylate (0.54 g, 3.2 mmoles) at room temperature under argon atmosphere. The reaction mixture after stirring for 10 hours evaporated to dryness. The residue was dissolved in dichloromethane (150 mL) and washed with 5% sodium bicarbonate (50 mL), water (50 mL) and brine (50 mL). The organic extract was dried over anhydrous sodium sulfate and evaporated to dryness. The residue was flash chromatographed over silica gel using dichloromethane/acetone (7:3) as the eluent. The pure fractions were collected together and evaporated to give 1.7 g (74%) of foam: $^1$H nmr (deuteriochloroform): δ1.04 (m, 3OH, 5 Isobutyl-$CH_3$), 1.68 (m, 2H, $CH_2CH_2CH_2$), 2.55 (m, 16H, 7 $CH_2$, $C_2$·H, & isobutyl-CH), 3.08 (m, 1H, $C_2$·H), 3.36 (m, 2H, $CH_2$), 3.52 (m, 8H, 4 $ArCH_2$), 3.84 (m, 1H, $C_4$·H), 4.00 (m, 2H, $C_5$·$CH_2$), 4.72 (m, 1H, $C_3$·H), 5.50 (s, 2H, $ArCH_2$), 6.18 (m, 1H, $C_1$·H), 7.04 (m, 1H, $N_2$H), 7.26 (m, 25H, ArH), 7.76 (s, 1H, $C_8$H).

Anal. Calcd. for $C_{70}H_{97}N_9O_6Si_2$: C, 69.09; H, 8.04; N, 10.36. Found: C, 69.12; H, 8.23; N, 10.19.

EXAMPLE 56

6-O-(Phenylmethyl)-N-[15-methyl-14-oxo-4,7,10,13 -tetrakis(phenylmethyl)-4,7,10,13-tetraazahexadec-1-yl]2'-deoxyguanosine (58).

To a stirred solution of compound 57 (5.0 g, 4.11 mmoles) in pyridine (50 mL) was added freshly prepared 1N solution of tetrabutylammonium fluoride (20 mL, 20 mmoles; prepared in a mixture of pyridine:tetrahydrofuran:water in the ratio of 5:4:1) at room temperature. The reaction mixture was allowed to stir for 30 minutes and quenched with H$^+$ resin (pyridinium form) to pH 6–7. The resin was filtered, washed with methanol (50 mL), and the combined filtrate evaporated to dryness. The residue was dissolved in dichloromethane (200 mL), washed with water (50 mL), and brine (50 mL). The organic extract was dried over sodium sulfate and concentrated to dryness. The foam that obtained was purified by flash chromatography over silica gel column using dichloromethane/methanol (95:5) as the eluent. The required fractions were collected together and evaporated to give 3.5 g (87%) of the titled compound as foam. $^1$H nmr (deuteriochloroform): δ1.04 (m, 30H, 5 isobutyryl $CH_3$), 1.68 (m, 2H, $CH_2CH_2CH_2$), 2.55 (m, 16H, 7 $CH_2$, $C_2$·H, & isobutyryl CH), 3.08 (m, 1H, $C_2$·H), 3.36 (m, 2H, $CH_2$), 3.52 (m, 8H, 4 $ArCH_2$), 3.84 (m, 1H, $C_4$·H), 4.00 (m, 2H, $C_5.CH_2$), 4.72 (m, 1H, $C_3.H$), 5.50 (s, 2H, $ArCH_2$), 6.18 (m, 1H, $C_1.H$), 7.04 (m, 1H, $N_2H$), 7.26 (m, 25H, ArH), 7.76 (s, 1H, $C_8H$).
Anal. Calcd. for $C_{70}H_{97}N_9O_6Si_2$: C, 69.09; H, 8.04; N, 10.36. Found: C, 69.12; H, 8.23; N, 10.19.
SCHEME 3
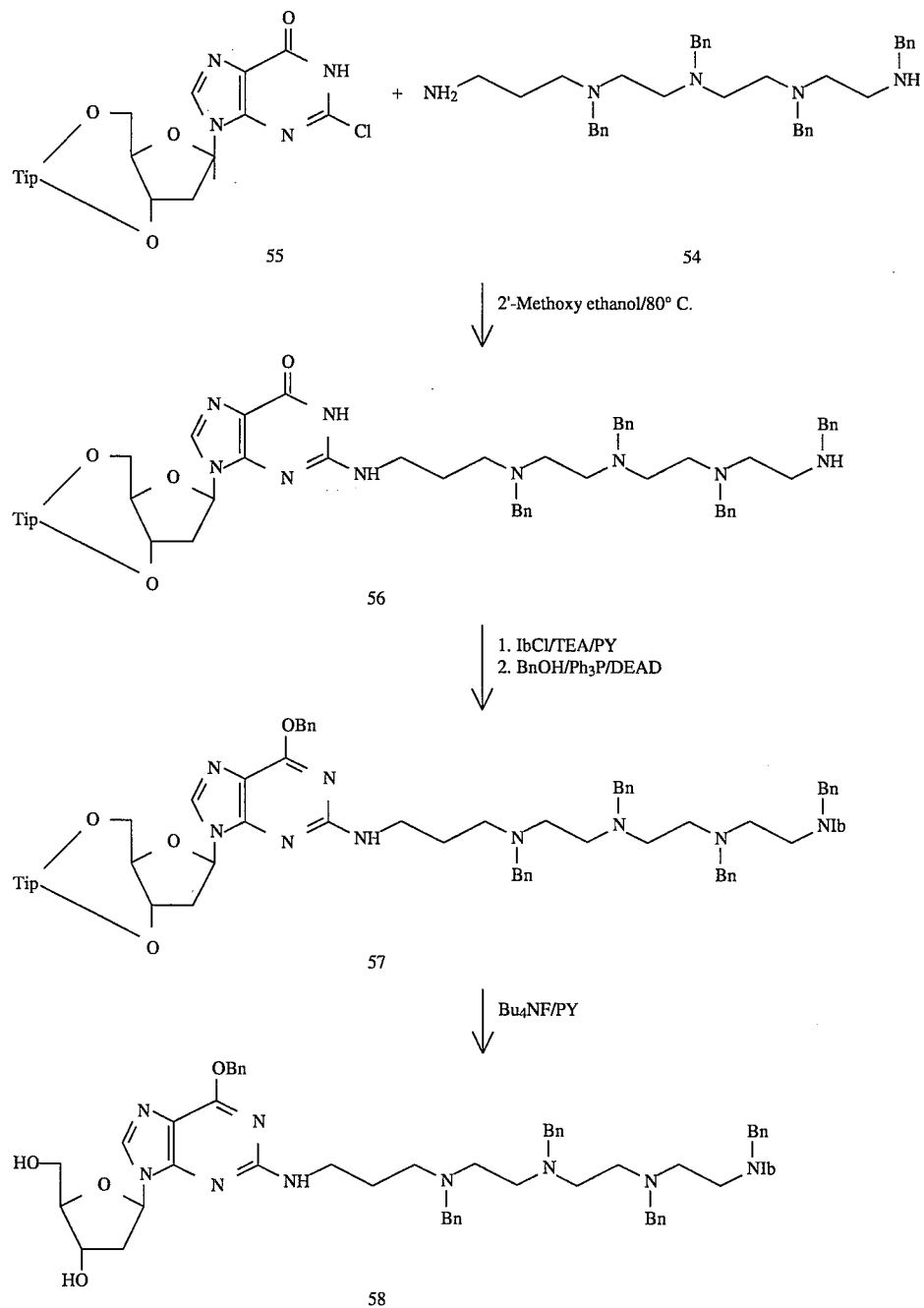

EXAMPLE 57

The amidites 9, 17, 23, 30, 35, 41 and 46, as discussed in the Detailed Description of the Preferred Embodiments, are incorporated into oligonucleotide sequences via automated DNA synthesis protocol. (Standard protocol using an ABI 380B DNA synthesizer was modified by increasing the wait step after the pulse delivery of tetrazole to 900 seconds. Deprotection conditions are discussed in Himmelsbach, et al., *Tetrahedron*, 1984, 40, 59). Enzymatic degradation and subsequent HPLC analysis indicated the expected ratios of the nucleoside components. (Oligonucleotides were digested with a mixture of spleen phosphodiesterase, snake venom phosphodiesterase, and bacterial alkaline phosphatase to provide individual nucleosides which were analyzed by HPLC).

A 21-mer oligonucleotide [5'd-(GCCGAGGTCCAT-GTCGTACGC)]was modified with one, three or seven $N^2$-[3-(1H-imidazol-1-yl(propyl)dGs or one or three $N^2$-[3-(1H-imidazol-1-yl)propyl]-2-$NH_2$ dAs and hybridized to complementary DNA or RNA. See Freier et al., *Gene Regulation: Biology of Antisense RNA and DNA*, (Erickson, et al. Raven Press, New York, 1992), pp. 95–107; Breslauer, et al., *Proc. Nat'l Acad. Sci. USA*, 1991, 8, 3746. Compared to unmodified DNA, the average change $T_m$/mod was +2.0 and +0.3 for dG modified oligonucleotides hybridized with DNA and RNA, respectively; the average change $T_m$/mod was +2.7 and +0.6 for dA modified oligonucleotides hybridized with DNA and RNA, respectively. The average enhancement of binding affinity of several different $N^2$-imidazolpropyl dG and $N^2$-imidazolpropyl-2-amino-dA modified oligonucleotides hybridized to DNA is 2.7 degrees Celsius/mod (3 different sequences, 16 incorporations) and 2.5 degrees Celsius/mod (3 different sequences, 12 incorporations), respectively. The relative specificity of hybridization of dG or $N^2$-imidazolpropyl dG to cytidine versus A, G, and U(T) mismatches of an RNA or DNA complement shows that $N^2$-modified dG is more specific to its complement cytidine than the corresponding unmodified dG; $N^2$-imidazolpropyl-2-$NH_2$ dA is as specific as dA against RNA or DNA. Incorporation of three $N^2$-imidazolpropyl-2-$NH_2$ dGs or 2-$NH_2$-dAs at the n-1, n-2, and n-3 positions at the 3' end of a 15-mer provided an increase in stability ($T_{1/2}$=9 and 16 h, respectively) to nucleolytic degradation in fetal calf serum compared to the unmodified oligomer ($T_{1/2}$=1 h). See Hoke et al., *Nucleic Acids Res.*, 1991, 8, 3746. The capped $N^2$-modified dG sequence was stabilized by 2.8 degrees Celsius/mod against DNA and 0.9 degrees Celsius against RNA, and the 2-$NH_2$-dA sequence was stabilized by 2.6 degrees Celsius/mod against DNA and 1.5 degrees/Celsius against RNA.

Molecular modeling simulations of oligomers containing the $N^2$-imidazolpropyl functionality suggest that the imidazole binds in the minor groove proximate to the phosphate backbone, stabilizing the DNA-DNA duplex. (Molecular minimization and dynamics studies were conducted using the Amber forcefield with the Insight and Discover programs (Biosys Inc., San Diego, Calif.). Four thousand steps of conjugate gradient minimization were used, followed by 1000 cycles of equilibration at 300 degrees Celsius, and 4000 steps of dynamics at 10 psec intervals). In the case of the RNA-DNA duplex, the imidazolpropyl group does not bind specifically since the minor groove is broad and the phosphates are turned away. However, other hydrogen bond donors and acceptors are accessible in the minor groove, which may account for the increased stability of the modified duplex.

A 21-mer having imidazolpropyl modified dG in 7 positions (1,4,6,7,13,16, and 20) and another 21-mer having imidazolpropyl modified 2-$NH_2$-dA in 5 positions (1,5,8,11, and 18) support HeLa cell extract RNase H dependent cleavage. Agrawal, et al., *Proc. Nat'l Acad. Sci. USA*, 1989, 87, 1401. Furthermore, a 17-met phosphorothioate containing a modified dG at the primary cleavage site of HeLa cell extract RNase H did not prevent cleavage by the enzyme. Monia, et al., *Biol. Chem.*, submitted 1992. These data suggest the heteroduplexes formed between $N^2$-imidazolpropyl dG or 2-$NH_2$-dA modified oligonucleotides and RNA are recognized by RNase H. The following Table 1 is illustrative of these studies.

TABLE 1

| MODIFIED OLIGONUCLEOTIDES AND THEIR HYBRIDIZATION PROPERTIES | | | | | |
| --- | --- | --- | --- | --- | --- |
| Sequences | Mod | $\Delta\Delta G°_{37}$ | Wild (Tm) | Mod (Tm) | $\Delta T_m$ | $\Delta T_m$/Mod |
| Against DNA | | | | | | |
| GCC TG'A TCA GGC* | 1 | −4.33 | 50.7 | 63.4 | +12.7 | +6.4 |
| GCC GAG GTC CAT G'TC GTA CGC | 1 | −0.25 | 69.7 | 72.3 | +2.6 | +2.6 |
| GCC G'AG GTC CAT G'TC GTA CG'C | 3 | +0.05 | 69.7 | 75.8 | +6.1 | +2.0 |
| G'CC G'AG' G'TC CAT G'TC G'TA CG'C | 7 | −4,30 | 69.7 | 83.3 | +13.6 | +1.9 |
| CGA CTA TGC AAG' G'G'C | 3 | −2.01 | 56.5 | 64.9 | +8.4 | +2.8 |
| CGA CTA TGC AAA' A'A'C | 3 | −2.86 | 50.5 | 58.1 | +7.6 | +2.6 |
| A'CC GA'G GA'T CA'T GTC GTA' CGC | 5 | −1.41 | 66.1 | 77.6 | +11.5 | +2.3 |
| GCC GA'G GTC CA'T GTC GTA' CGC | 3 | +1.31 | 69.7 | 77.6 | +7.9 | +2.6 |
| GCC GAG GTC CA'T GTC GTA CGC | 1 | +3.10 | 69.7 | 72.4 | +2.7 | +2.7 |
| aCC GaG GTC CaT GTC GTa CGC | 5 | +0.49 | 66.1 | 69.2 | +3.09 | +0.6 |
| GCC GAG GTC CaT GTC GTA CGC | 1 | +2.15 | 69.7 | 70.9 | +1.25 | +1.3 |
| Against RNA | | | | | | |
| GCC GAG GTC CAT G'TC GTA CGC | 1 | −0.39 | 69.1 | 69.6 | +0.5 | +0.5 |
| GCC G'AG GTC CAT G'TC GTA CG'C | 3 | −0.15 | 69.1 | 70.3 | +1.2 | +0.4 |
| G'CC G'AG' G'TC CAT G'TC G'TA CG'C | 7 | +3.10 | 69.1 | 70.4 | +1.3 | +0.2 |
| CGA CTA TGC AAA' A'A'C | 3 | −1.24 | 39.0 | 43.4 | +4.4 | +1.5 |
| A'CC GA'G GA'T CA'T GTC GTA' CGC | 5 | +1.59 | 63.2 | 65.9 | +2.7 | +0.5 |
| GCC GA'G GTC CA'T GTC GTA' CGC | 3 | +2.86 | 69.1 | 71.2 | +2.1 | +0.7 |
| GCC GAG GTC CA'T GTC GTA CGC | 1 | +3.41 | 69.1 | 69.5 | +0.4 | +0.4 |

*Self Complementary; A' = $N_2$-Imidazolylpropyl dA; G' = $N_2$-Imidazolylpropyl dG

EXAMPLE 58

Chromatography and Purification.

Silica gel used for flash chromatography was ICN 60 (Costa Mesa, Calif.), 32–63 mesh. Materials not soluble in the solvent system used for flash chromatography (FC) were coevaporated onto E. Merck silica gel 100 (Darmstadt, Republic of Germany), 70–230 mesh, using a suitable solvent. The dry materials were then applied to the top of a FC column. TLC was performed on prescored E. Merck Kieselgel 60 $F_{254}$ plates. Compounds were visualized by illuminating TLC plates under UV light (254 nm) and/or by spraying with 10 methanolic $H_2SO_4$ followed by heating. Evaporations were carried out at 40°–50° C. using a rotary evaporator and a vacuum pump coupled to a vacuum controller. $^1$H-NMR spectra were obtained at 400 mHz in dmso-$d_6$ unless otherwise noted. Where relevant, treatment of samples with $D_2O$ recorded exchangeable protons. Infrared spectra were recorded on a Perkin-Elmer 16PC FT-IR spectrophotometer. Solvent system A=ethyl acetate-hexanes, 3:2; B=ethyl acetate-methanol, 9:1, v/v.

EXAMPLE 59

Procedure for attaching modified 5'-dimethoxytriphenylmethyl ribonucleosides to the 5'-hydroxyl of nucleosides bound to CPG support.

The modified nucleosides that will reside in the terminal 3'-position of certain oligonucleotides are protected as their 5'-DMT (the cytosine and adenine exocyclic amino groups are benzoylated and the guanine amino is isobutyrlated) and treated with trifluoroacetic acid/bromoacetic acid mixed anhydride in pyridine and dimethylaminopyridine at 50° C. for five hours. The solution is evaporated under reduced pressure to a thin syrup which is dissolved in ethyl acetate and passed through a column of silica gel. The homogenous fractions were collected and evaporated to dryness. A solution of 10 mL of acetonitrile, 10 micromoles of the 3'-O-bromomethyl-ester modified pyrimidine nucleoside, and one mL of pyridine/dimethylaminopyridine (1:1) is syringed slowly (60 to 90 sec) through a one micromole column of CPG thymidine (Applied Biosystems, Inc.) that had previously been treated with acid according to standard conditions to afford the free 5'-hydroxyl group. Other nucleosides bound to CPG columns could be employed. The eluent is collected and syringed again through the column. This process is repeated three times. The CPG column with 10 mL of acetonitrile and then attached to an ABI 380B nucleic acid synthesizer. Oligonucleotide synthesis is now initiated. The standard conditions of concentrated ammonium hydroxide deprotection that cleaves the thymidine ester linkage from the CPG support also cleaves the 3',5' ester linkage connecting the pyrimidine modified nucleoside to the thymidine that was initially bound to the CPG nucleoside. In this manner, any modified nucleoside or generally any nucleoside with modifications in the heterocycle and/or sugar can be attached at the 3' end of an oligonucleotide sequence.

EXAMPLE 60

Procedure for the conversion of modified nucleoside-5'-DMT-3'-phosphoramidites into oligonucleotides.

The polyribonucleotide solid phase synthesis procedure of Sproat, et al., 1989, *Nucleic Acids Res.*, 17, 3373–3386 is used to prepare the modified oligonucleotides.

EXAMPLE 61

Preparation of Modified Phosphorothioate Oligonucleotides.

Substituted 5'-DMT nucleoside 3'-phosphoroamidites prepared as described in the above Examples are inserted into sequence specific oligonucleotide phosphorothioates as described by Sproat, supra, at 3373–3386 and Beaucage, et al., *J. Am. Chem. Soc'y*, 1989, 112, 1253–1255.

What is claimed is:

1. A compound having the formula:

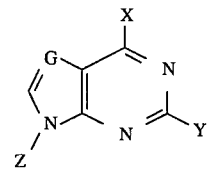

wherein

G is CH or N;

X is $NH_2$ or OH;

Y is RQ or NHRQ, wherein said R is a hydrocarbyl group having from 2 to about 20 carbon atoms; and Q is H, $NH_2$, polyalkylamino, hydrazines, hydroxylamines, imidazoles, imidazole amides, alkylimidazoles, tetrazole, triazole, or alkoxy groups; and Z is ribose or deoxyribose.

2. The compound of claim 1 wherein Q is imidazole, imidazole amide, alkyimidazole, tetrazole, or triazole.

3. The compound of claim 1 wherein Q is imidazole, an imidazole amide or an alkylimidazole.

4. The compound of claim 1 wherein Y is RQ, said Q is an imidazole.

5. The compound of claim 1 wherein Y is NHRQ, said Q is an imidazole.

6. The compound of claim 1 wherein G is N; X is $NH_2$; Y is NHRQ, said R is a lower alkane; and Q is an imidazole.

7. The compound of claim 6 wherein said R is an alkane having from 2 to about 4 carbon atoms.

8. The compound of claim 6 wherein R is propyl.

9. The compound of claim 1 wherein G is N; X is OH; Y is NHRQ, said R is a lower alkane; and Q is an imidazole.

10. The compound of claim 9 wherein R is an alkane having from 2 to about 4 carbon atoms.

11. The compound of claim 9 wherein R is propyl.

12. The compound of claim 9 wherein R is ethyl.

13. The compound of claim 1 wherein G is N; X is $NH_2$; Y is NHRQ, said Q is H and R is an alkane having from about 5 up to about 20 carbon atoms.

14. The compound of claim 1 wherein G is N; X is OH; Y is NHRQ, said Q is H and R is an alkane having from about 5 up to about 20 carbon atoms.

15. The compound of claim 14 wherein R is nonyl.

16. The compound of claim 1 wherein Y is RQ, said R is a lower alkane; and Q is an amine, wherein said amine is selected form the group consisting of $NH_2$, polyalkylamine, aminoalkylamino, hydrazine (—NH—NH—), or hydroxylamine(—NH—OH).

17. The compound of claim 1 wherein Y is NHRQ, said R is a lower alkane; and Q is an amine, wherein said amine is selected from the group consisting of $NH_2$, polyalkylamine, aminoalkylamine, hydrazine (—NH—NH—), or hydroxylamine (—NH—OH).

18. The compound of claim 1 wherein G is N; X is $N_2$; Y is NHRQ, said R is a lower alkane; and Q is an amine, wherein said amine is selected from the group consisting of $NH_2$, polyalkylamine, aminoalkylamine, hydrazine (—NH— NH—), or hydroxylamine (—NH—OH).

19. The compound of claim 18 wherein said amine is $NH_2$.

20. The compound of claim 1 wherein G is N; X is OH;

Y is NHRQ, said R is a lower alkane; and Q is an amine, wherein said amine is selected from the group consisting of NH₂, polyalkylamine, aminoalkylamines, hydrazines (—NH—NH—), or hydroxylamines (—NH—OH).

21. The compound of claim 20 wherein said amine is NH₂.

22. The compound of claim 20 wherein R is hexane and Q is NH₂.

23. The compound of claim 1 wherein Y is NHRQ, said Q is an alkoxy group.

24. The compound of claim 1 wherein Y is RQ, said Q is an alkoxy group.

25. The compound of claim 1 further having a phosphate group at the 3' position of the ribose or deoxyribose.

26. The compound of claim 25 wherein said phosphate is a methylphosphonate, phosphorothioate, phosphoramidite, or phosphorotriester.

27. A compound having the formula:

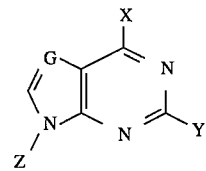

wherein
G is CH or N;
X is NH₂ or OH;
Y is R-aminoalkylamino or NHR-aminoalkylamino, wherein said R is a hydrocarbyl group having from 2 to about 20 carbon atoms; and Z is ribose or deoxyribose.

* * * * *

UNITED STATES PATENT AND TRADEMARK OFFICE
CERTIFICATE OF CORRECTION

PATENT NO. : 5,459,255
DATED : October 17, 1995
INVENTOR(S) : P. Dan Cook, Kanda S. Ramasamy, Muthia Manoharan It is certified that error appears in the above-indentified patent and that said Letters Patent is hereby corrected as shown below:

Column 29, Line 40, please delete "$5.61$" and insert --5.61-- therefor.

Signed and Sealed this

Sixteenth Day of June, 1998

Attest:

BRUCE LEHMAN

Attesting Officer

Commissioner of Patents and Trademarks